(12) United States Patent
Pollack

(10) Patent No.: US 9,684,006 B2
(45) Date of Patent: Jun. 20, 2017

(54) SURFACE MARKINGS FOR AN OPTICALLY GUIDED DEVICE

(71) Applicant: Siemens Healthcare Diagnostics Inc., Tarrytown, NY (US)

(72) Inventor: Benjamin S. Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/773,170

(22) PCT Filed: Mar. 7, 2014

(86) PCT No.: PCT/US2014/021555
§ 371 (c)(1),
(2) Date: Sep. 4, 2015

(87) PCT Pub. No.: WO2014/138530
PCT Pub. Date: Sep. 12, 2014

(65) Prior Publication Data
US 2016/0011224 A1    Jan. 14, 2016

Related U.S. Application Data

(60) Provisional application No. 61/775,077, filed on Mar. 8, 2013.

(51) Int. Cl.
*G06K 7/10* (2006.01)
*G01N 35/00* (2006.01)
(Continued)

(52) U.S. Cl.
CPC ....... *G01N 35/00732* (2013.01); *B65G 43/08* (2013.01); *G01N 35/02* (2013.01);
(Continued)

(58) Field of Classification Search
CPC .. G06K 7/10; G06K 9/18; G06K 7/04; G06K 7/00; G06K 9/36; G06F 17/00; G06F 7/00
(Continued)

(56) References Cited

U.S. PATENT DOCUMENTS

2005/0134461 A1 * 6/2005 Gelbman ........... G06K 7/10079
340/572.8
2006/0118738 A1    6/2006 Ross et al.
(Continued)

FOREIGN PATENT DOCUMENTS

WO    2012/158520 A1    11/2012

OTHER PUBLICATIONS

PCT International Search Report and Written Opinion dated Sep. 9, 2014 (10 Pages).

*Primary Examiner* — Edwyn Labaze

(57) ABSTRACT

Methods and systems for use with an automation system in an automated clinical chemistry analyzer can include one or more surfaces configured to dynamically display a plurality of optical marks, a plurality of independently movable carriers configured to move along surfaces and to observe them to determine navigational information from the plurality of optical marks, and a processor configured to update the plurality of optical marks to convey information that pertains to each respective independently movable carrier. The plurality of marks can include two-dimensional optically encoded marks, barcodes oriented in a direction of travel of the carriers, marks that dynamically convey data, dynamic lines configured to be followed by the carriers, marks indicating a collision zone, or dynamic marks displayed at a location coincident with the location of a pipette.

21 Claims, 25 Drawing Sheets

(51) Int. Cl.
  *G01N 35/04* (2006.01)
  *B65G 43/08* (2006.01)
  *G01N 35/02* (2006.01)
(52) U.S. Cl.
  CPC ...... *G01N 35/04* (2013.01); *B65G 2811/0678* (2013.01); *G01N 2035/00752* (2013.01); *G01N 2035/0406* (2013.01)
(58) Field of Classification Search
  USPC ..... 235/462.09, 375, 376, 438, 446, 462.01, 235/487
  See application file for complete search history.

(56) References Cited

U.S. PATENT DOCUMENTS

| | | | |
|---|---|---|---|
| 2007/0030152 A1 | 2/2007 | Sprague | |
| 2009/0158863 A1 | 6/2009 | Shanafelter | |
| 2013/0245810 A1* | 9/2013 | Sullivan | G06Q 10/08 700/214 |
| 2013/0310969 A1* | 11/2013 | Terzini | G06F 19/3462 700/235 |
| 2014/0305227 A1* | 10/2014 | Johns | B01D 21/262 73/863.01 |

* cited by examiner

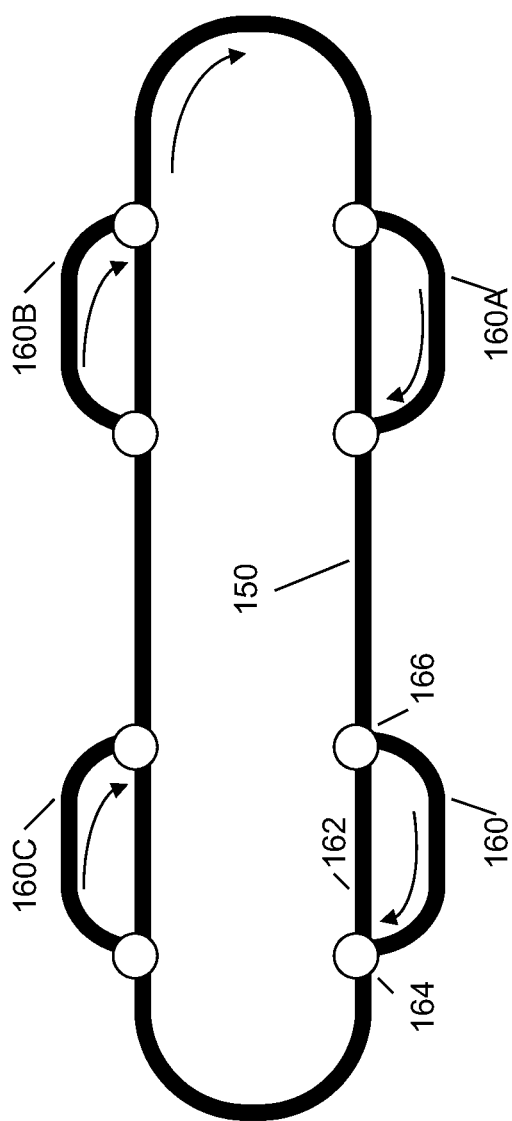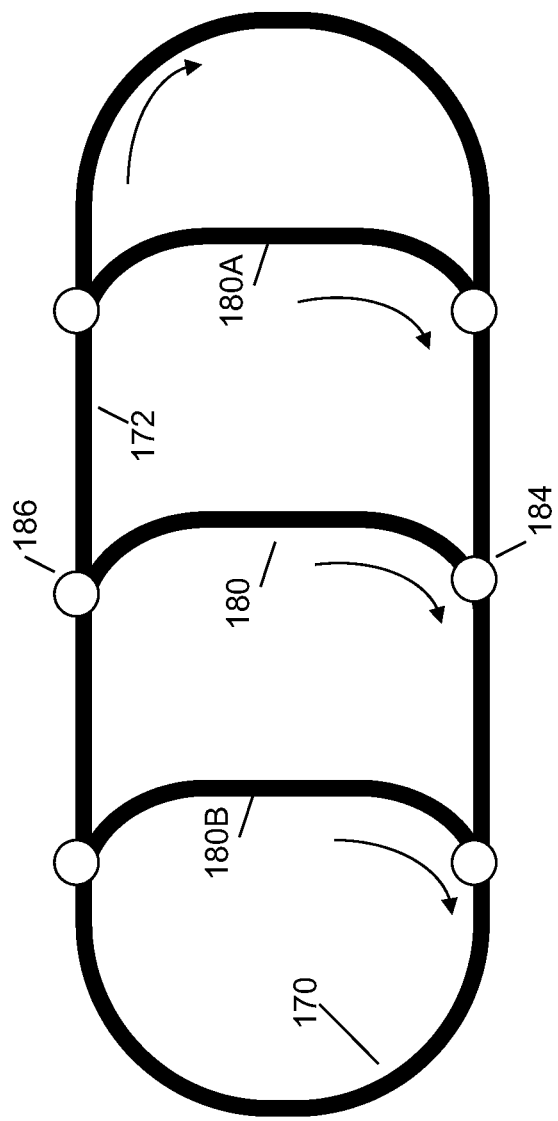

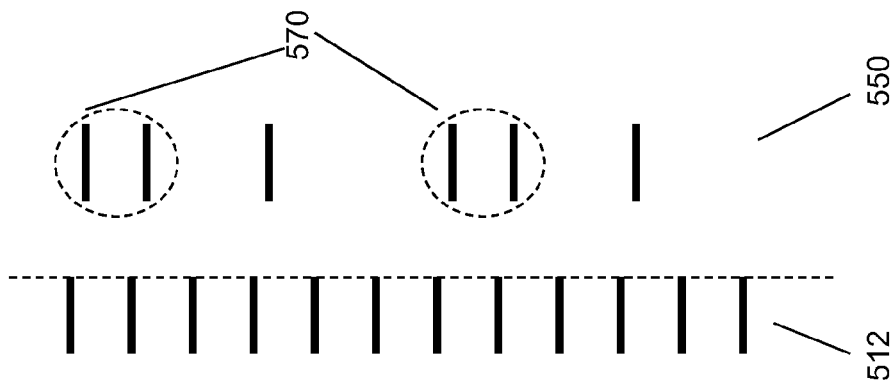
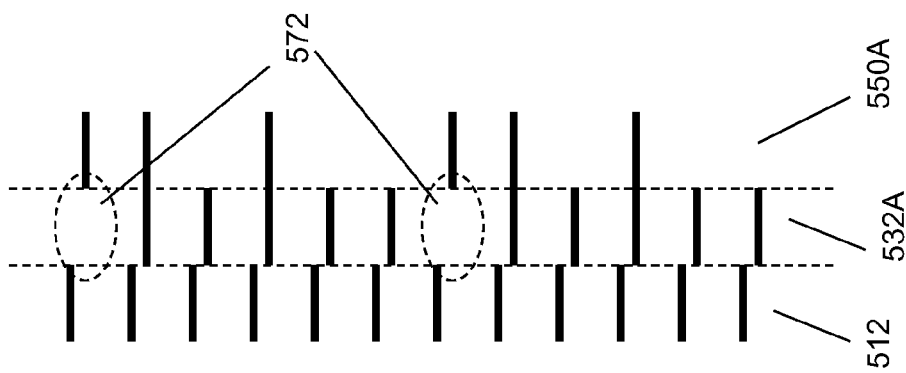
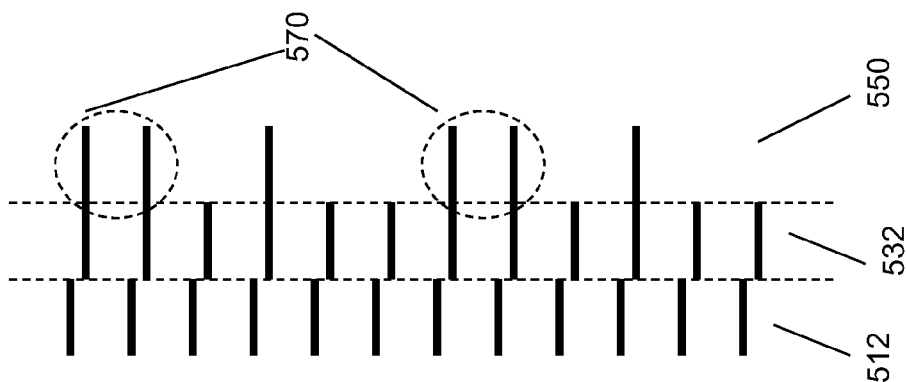

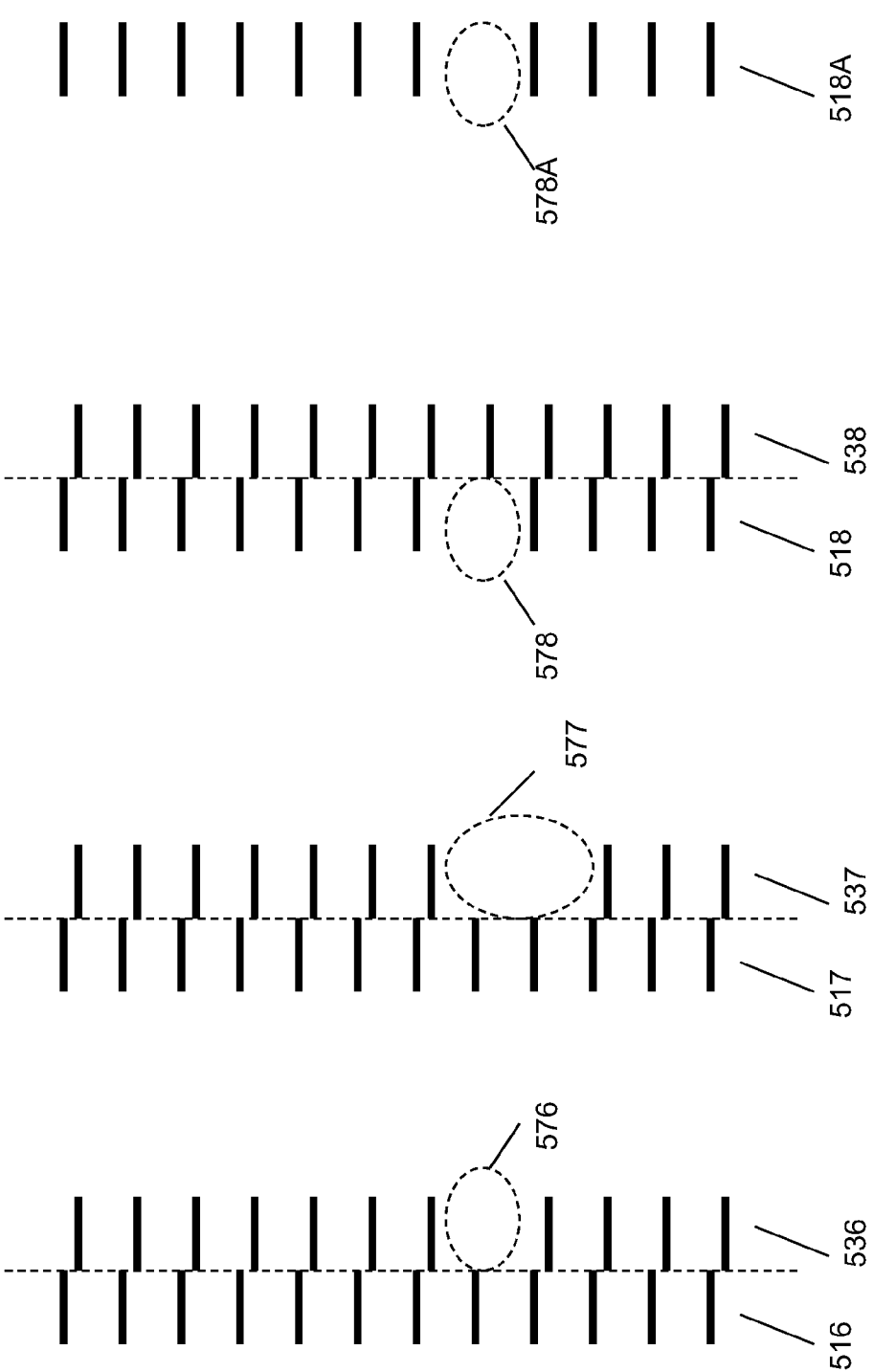

SURFACE MARKINGS FOR AN OPTICALLY GUIDED DEVICE

CROSS-REFERENCE TO RELATED APPLICATIONS

This application claims priority to U.S. provisional application Ser. No. 61/775,077 filed Mar. 8, 2013, which is incorporated herein by reference in its entirety.

TECHNOLOGY FIELD

The present invention relates in general to an automation system for use in a laboratory environment and, more particularly, to systems and methods for transporting fluid containers (e.g., vessels holding patient samples) for in vitro diagnostics (IVD) in a clinical analyzer via active transport devices. Embodiments of the present invention are particularly well suited for, but in no way limited to, optical encoding for conveying local position information to independent carriers having active direction and routing capabilities.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some prior art systems, a modular approach is used for analyzers. A lab automation system can shuttle samples between one modular testing station (e.g., a unit that can specialize in certain types of assays or can otherwise provide testing services to a larger analyzer) and another. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths (sometimes called sidecars or pullouts). A drawback with this configuration is that singulation, which is often slow, must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track.

Another way that singulation has been used in friction track-based systems is to stop the puck at a gate and allow a barcode reader to read a barcode on the sample tube. Because barcode readers are slow relative to the amount of time needed to switch a puck between tracks, scanning introduces hard singulations into the flow on a track and causes all nearby pucks to halt while a switching determination is made. After a determination is made, singulation may be further used to ensure that only the scanned puck proceeds by using a physical blockage to prevent the puck behind the scanned puck from proceeding, while the scanned puck is switched.

U.S. Pat. No. 6,202,829 shows an exemplary prior art friction track system that includes actuated mechanical diversion gates that can be used to direct pucks off of the main track onto pullout tracks. As explained therein, the diversion process can require multiple mechanical gates to singulate and separate individual pucks, stopping each puck multiple times and allowing each puck to be rotated so that a barcode can be read before a diversion decision is made. Such a system increases latency and virtually ensures that each time a diversion gate is added to a friction track, the gate adds another traffic bottleneck. Such a system results in natural queuing at each diversion gate, further increasing the amount of time that each sample spends on the friction track.

While there has been some development of autonomous transport carriers outside the IVD environment, such as industrial and shipping environments, there has yet to be an effective system that uses independently routable and positionable carriers in an IVD setting. One reason for the lack of automated carriers may include the need for precise positioning of vessels holding samples or reagents in relation to stations, such as testing stations or other sample handling stations. For example, a carrier must be able to reliably position itself at a destination to within about a centimeter to allow aspiration of the sample carried. Similarly, the small size needed for carriers in an IVD setting and relatively small size of features of tracks used to transport samples present challenges in adapting systems and techniques used in industrial systems. Furthermore, in an IVD environment, automation systems have traditionally favored reliability over complexity, favoring passive carriers, rather than the added complexity of active carriers.

SUMMARY

Embodiments of the present invention address and overcome one or more of the above shortcomings and drawbacks by providing devices, systems, and methods for providing location and trajectory information for use by intelligent carriers that transport samples. This technology is particularly well-suited for, but by no means, limited to transport mechanisms in an automation system for use in an in vitro diagnostics (IVD) environment.

According to at least one embodiment, an automation system for use with an automated clinical chemistry analyzer can include one or more surfaces configured to dynamically display a plurality of optical marks, a plurality of independently movable carriers configured to move along surfaces and to observe them to determine navigational information from the plurality of optical marks, and a processor configured to update the plurality of optical marks to convey information that pertains to each respective independently movable carrier.

According to one aspect of some embodiments, the plurality of marks can include at least one two-dimensional optically encoded mark, at least one barcode oriented in a direction of travel of the plurality of independently movable carriers, marks that dynamically convey data to the plurality of independently movable carriers, and/or at least one line configured to be followed by one or more of the plurality of independently movable carriers, wherein the line changes to dynamically instruct each carrier to move in a predetermined direction. The plurality of marks may also include marks indicating a collision zone of at least one of the plurality of independently movable carriers and/or marks that are dynamically displayed on one of the track surfaces at a location coincident with the location of a pipette.

According to another aspect of some embodiments, at least one of the one or more surfaces is substantially unconstrained in two dimensions, facilitating arbitrary two-dimensional movement defined by the at least one line. The one or more surfaces may be further configured to statically display a plurality of static optical marks.

According to another aspect of some embodiments, each of the plurality of independently movable carriers can include one or more optical sensors and at least one processor configured to control the motion of the carrier in response to the plurality of optical marks.

According to at least one embodiment, a carrier that is configured to travel along an automation surface for use with an automated clinical chemistry analyzer can include one or more optical sensors for observing a plurality of optical marks on the automation surface and at least one processor configured to determine navigational information from the optical marks and to control the trajectory of the carrier in response to the optical marks.

According to at least one aspect of some embodiments, the processor can be further configured to receive non-positional data from the optical marks, to control the carrier to follow a dynamic line or to determine if the carrier is at risk of colliding with another carrier from the optical marks.

According to another aspect of some embodiments, the carrier may be configured to observe one or more marks on the first surface to determine a stopping point in the automation surface. The carrier may also be configured to observe one or more synchronization marks on the first surface of the track. Furthermore, the carrier may lack an RF receiver for receiving information from an automation system. The carrier may also include an RFID tag to identify it to an automation system.

According to at least one embodiment, an automation system for use with an automated clinical chemistry analyzer can include a plurality of track sections configured to facilitate travel between a plurality of locations in the automation system, a plurality of electronically rewriteable surfaces configured to dynamically display navigational marks to a plurality of carriers that traverse the automation system, and at least one or more optical sensors and RFID scanners configured to determine at least the current track section of the plurality of carriers. The automation system may further include one or more processors configured to update information displayed by the electronically rewriteable surfaces to convey individualized information to individual carriers as they traverse the automation system, including information to instruct carriers where to go in the automation system.

According to at least one aspect of some embodiments, the plurality of electronically rewriteable surfaces includes an LCD or e-ink display. According to another aspect of some embodiments, the automation system includes a characterization station configured to characterize the location of a sample being carried by each carrier relative to the rest of the carrier.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIGS. 9A-9D are surface views of markings on exemplary track sections for use with embodiments of an encoding scheme;

FIGS. 10A-10D are surface views of markings on exemplary track sections for use with embodiments of an encoding scheme;

DETAILED DESCRIPTION OF ILLUSTRATIVE EMBODIMENTS

Figure 1:
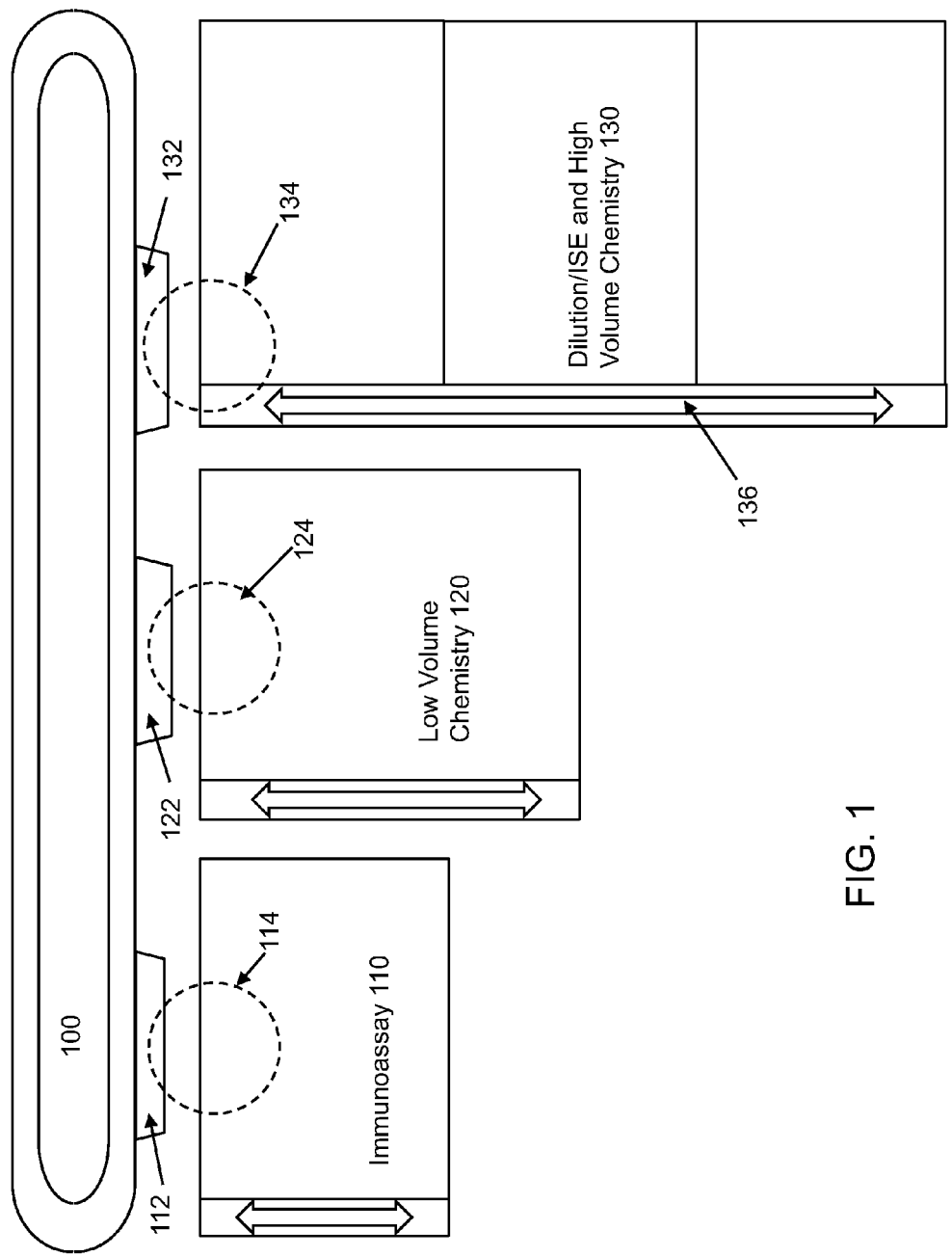
FIG. 1 is a top view of an exemplary clinical chemistry analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Carriers/Trays/Racks: A carrier may be distinguishable from a tray, which may commonly refer to a device that does not travel along an automation track (e.g., carried by an operator) and is configured to hold a plurality of payloads (e.g., sample tubes). A rack is a general term to describe a device that is configured to hold a plurality of payloads (e.g., sample tubes). A rack may refer to a tray (when used outside an automation track) or carrier (when configured to traverse an automation track) that is configured to carry a plurality of payloads. Racks may refer to one-dimensional or two-dimensional arrays of slots, in some embodiments.

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. IVD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

The above problems in the prior art have motivated the discovery of improved apparatus and methods for reliably and/or automatically transporting samples between stations/testing modules within an automated clinical analyzer (analyzer). Specifically, by providing encoded distance or position marks on a track surface, semi-autonomous, independently movable carriers having imaging devices can be used to reliably transport samples, such as, for example, patient fluid samples in an in vitro diagnostics (IVD) clinical analyzer. These carriers can be configured to transport samples substantially faster than prior methods, allowing reliable scheduling of tests, a reduction of traffic in the automation system, and reduced latency and reliable throughput of tests within the analyzer. Some embodiments exploit the semi-autonomy of the sample carriers to provide transit between stations in less than a single operation cycle, effectively removing or greatly reducing automation of sample placement as a performance bottleneck, and allowing more flexible sample scheduling options. The rapid motion can create difficulty in reckoning the position of a carrier with sufficient accuracy in an IVD environment. By providing marks on a track surface, a carrier can determine a reference position when passing a position mark and then observe the relative motion of a surface of the track to determine its current real-time position within the track. Additional synchronization marks can be provided on the track surface to calibrate the real-time positioning and trajectory, and prevent positioning or trajectory errors from accumulating between reference position marks. Marks may be provided on a track by providing marks on, in, within, or along a surface as described herein.

Embodiments of the present invention include systems and methods that provide a more efficient lab automation system to allow samples to be shuttled between and amongst various analyzer stations, including testing stations and sample handling stations, with less latency and more individual control. Embodiments of the present invention can reduce or eliminate queues experienced by samples traversing the automation system. Usually, samples need to undergo many different types of testing in an automated chemical analyzer, which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a chemical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system. Stations can also include pre-analytic stations or post-analytic stations. For example, a sample handling station may act as a pre-analytic station that decaps, mixes, verifies quality, or otherwise prepares a sample for analytic testing stations. A post-analytic station can include similar stations that sort and prepare a sample to be stored. It should be appreciated that the automation systems described herein may be suitable for transport within and amongst any of the available stations within the analyzer or throughout the IVD environment.

An exemplary track geometry, typical in prior art configurations, is shown in FIG. 1. This track can include prior art friction tracks, which may introduce challenges in designing a track system. However, certain embodiments of the present invention could also use a similar geometry without necessarily employing a friction track for motion. Track 100 can be a generally oval-shaped track that conveys samples in pucks or trays between various analyzing/testing stations 110, 120, and 130. Track 100 could be a single direction track or, in some instances, a linear bidirectional track. In this exemplary set-up, each analyzer 110, 120, and 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling a pending sample in pullout 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station or stations 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and, thus, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer/testing stations or sample handling stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples, can be placed in a container or vessel, such as a test tube, vial, cuvette, etc. that can be transported by a carrier. Carrier, and by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, and 160C as described herein. By way of example, if a sample carrier is traversing the main path 150 and reaches decision point 166, it can be made to continue on the main track to segment 162 or can be made to divert to sidecar 160. The systems and methods by which the decision can be made to divert the sample at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track portion 172 or be diverted onto path 180. Once an analyzer station along handling path 180 is done processing the sample, the sample proceeds to decision point 184 where it may be placed back onto the main path 170.

Figure 3:
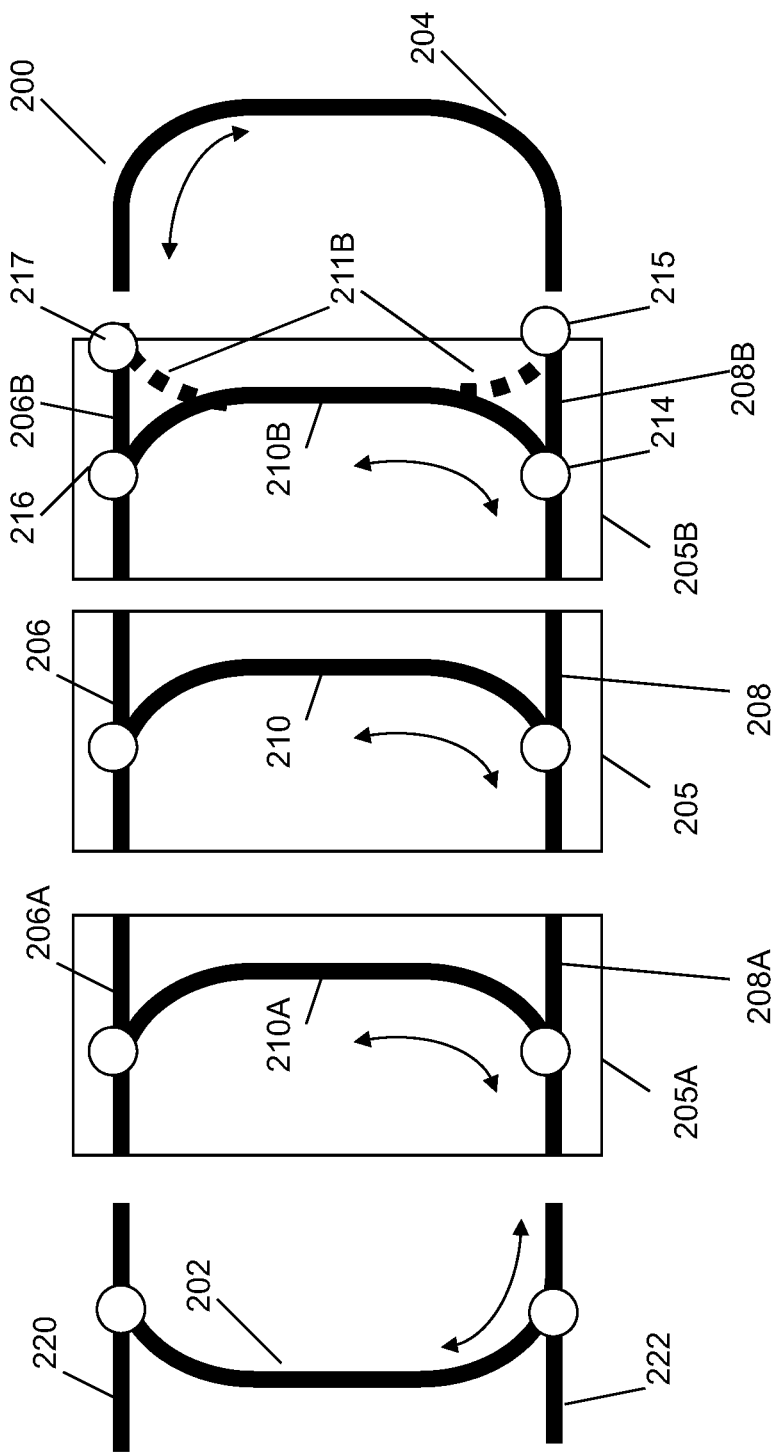
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B, respectively, form pullouts from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing, while allowing the other module to immediately process the sample on the next operation cycle. As used herein, an operation cycle is a unit of time used by scheduling algorithms to allot processing time to modules for sample assays. These can be dynamic or fixed, and can allow synchronous operation of the modules in the analyzer and provide a reliable timing model for scheduling samples amongst multiple modules in the analyzer. The operation cycle time can be chosen to be the time needed by any given module between when it starts processing a first sample and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post-analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while, in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module a prior knowledge of the arrival time of a sample, each module can prepare resources and interleave tests or portions of tests to more efficiently allot internal resources. In this manner, modules can operate on samples in a just-in-time manner, rather than using large physical buffers. The effect is that the virtual queue for a given module can be much larger than the physical capacity of the sub-path serving that module and existing scheduling algorithms can be used. Effectively, each module can treat track 200 as it would treat a sample carousel in a prior art module.

It should also be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto the track 200. When the reagents on track 200 reach the appropriate module, the module can utilize mechanical systems such as an arm or a feeder system that takes the reagents off of the track and places the reagents in the reagents store for the module.

In some embodiments, the individual track portions shown in FIGS. 3, 2A and 2B can be operated independently from one another, or can be passive. Independent carrier movement provides advantages over friction-based track systems, such as non-localized conveyor belts, where the entire friction track must be moved to effect movement of a sample carrier. This means that other samples also on that track must move at the same rate. This also means that if certain sections operate at different speeds, collisions between passive carriers carrying samples can occur.

Figure 4A:
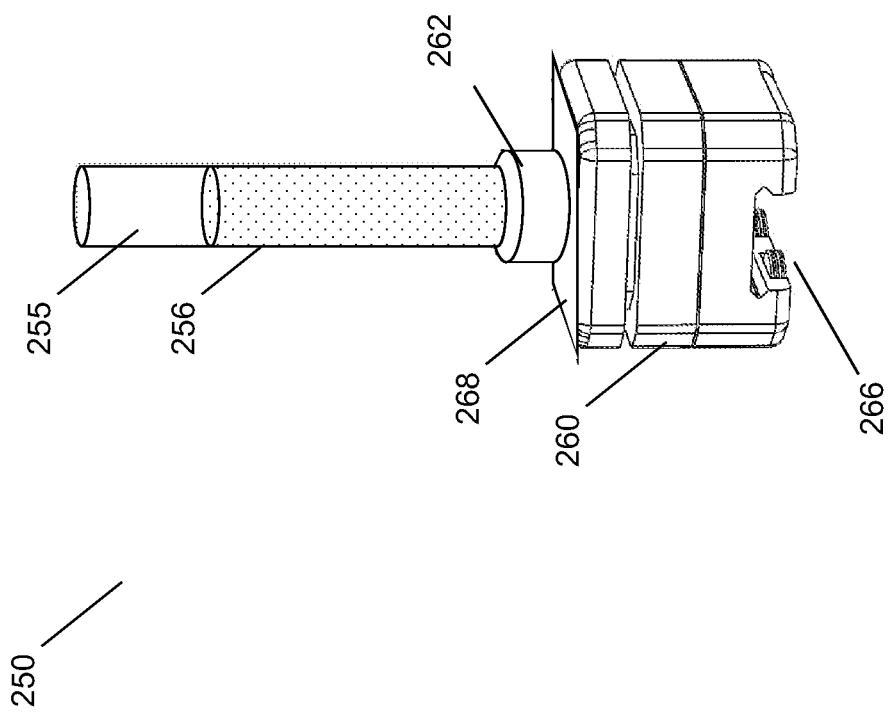
FIG. 4A is a perspective view of an exemplary carrier that can be used with the embodiments disclosed herein.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges, or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion 266 allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils. In some embodiments, the guide portion 266 can be physically constrained by the track, such that the range of motion is substantially bidirectional within the track and one-dimensional within the reference frame of the track (i.e., the motion is restricted transversely so that the carrier 250 can only move forward or backward along the track, even though the track may itself be two or three-dimensional). In some embodiments, the guide portion 266 can be less constrained laterally (e.g., more like a car on a road than a train on a track), such that the carrier 250 can control its lateral position, such as via a steering mechanism. In these embodiments, a carrier 250 can vary its position in two dimensions relative to the track. It will be appreciated that embodiments of two-dimensional position marks can be useful for facilitating the positioning of a carrier 250 in one or two dimensions.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
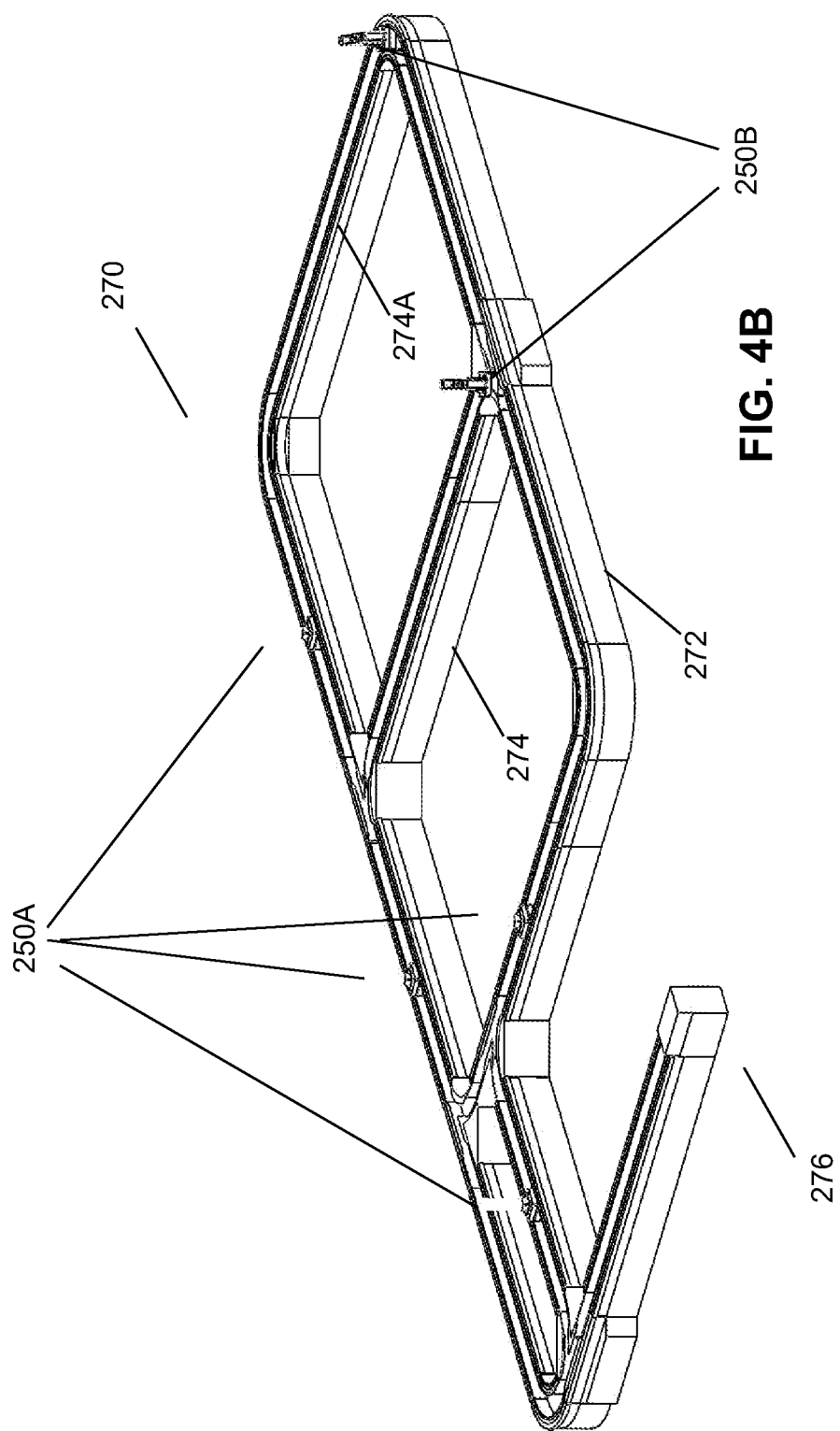
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or sub-paths 274 and 274A. Path 276 can be used by an operator to place samples into carriers or remove samples from these carriers.

Figure 4C:
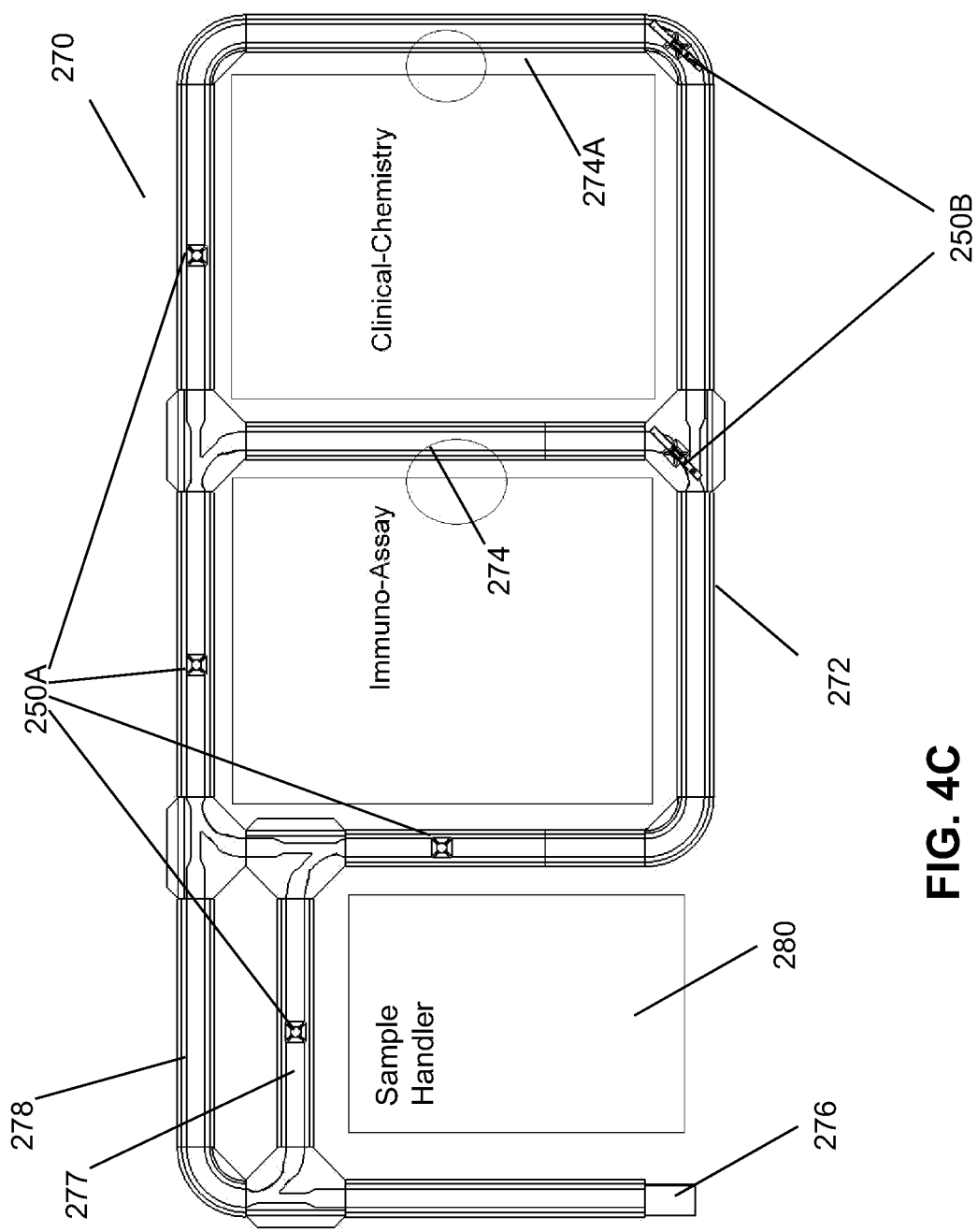
FIG. 4C is a top view of an exemplary track configuration that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub paths 277 and 278 to buffer samples for insertion or removal of the samples from the main track 272.

In some embodiments, the sample handler 280 can also load and unload samples or other payload to/from the carriers 250A and 250B. This allows the number of carriers to be reduced to the amount needed to support payloads that are currently being used by the stations in track system 270, rather than having a vast majority of carriers sitting idle on tracks 278 and 277 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas prior art lab automation systems utilize passive pucks or trays (e.g., the puck is a simple plastic or rubber brick that lacks active or autonomous systems, power, onboard processing, or control) to reduce cost and complexity, in some embodiments, the added complexity and cost necessary to integrate intelligence and autonomy into individual carriers (which can include intelligent pucks or trays in some embodiments) can provide benefits. Some embodiments can utilize intelligent independent carriers to enable certain improvements over passive pucks on friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior art friction-based track systems, the velocity of the track is typically limited to prevent acceleration and jerk experienced by pucks from exceeding threshold amounts because the entire track moves. However, in some embodiments, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section, as appropriate, resulting in a substantially higher average speed around the track. This can assist the carrier in traversing the entire track system in less than one machine cycle of the analyzer. These machine cycles can be, for instance, 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow the carrier to determine where it is on the track and where it needs to go, rather than being directed by the track (although, in some embodiments a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and image sensor, and can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go and, optionally, when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths, as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in U.S. Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
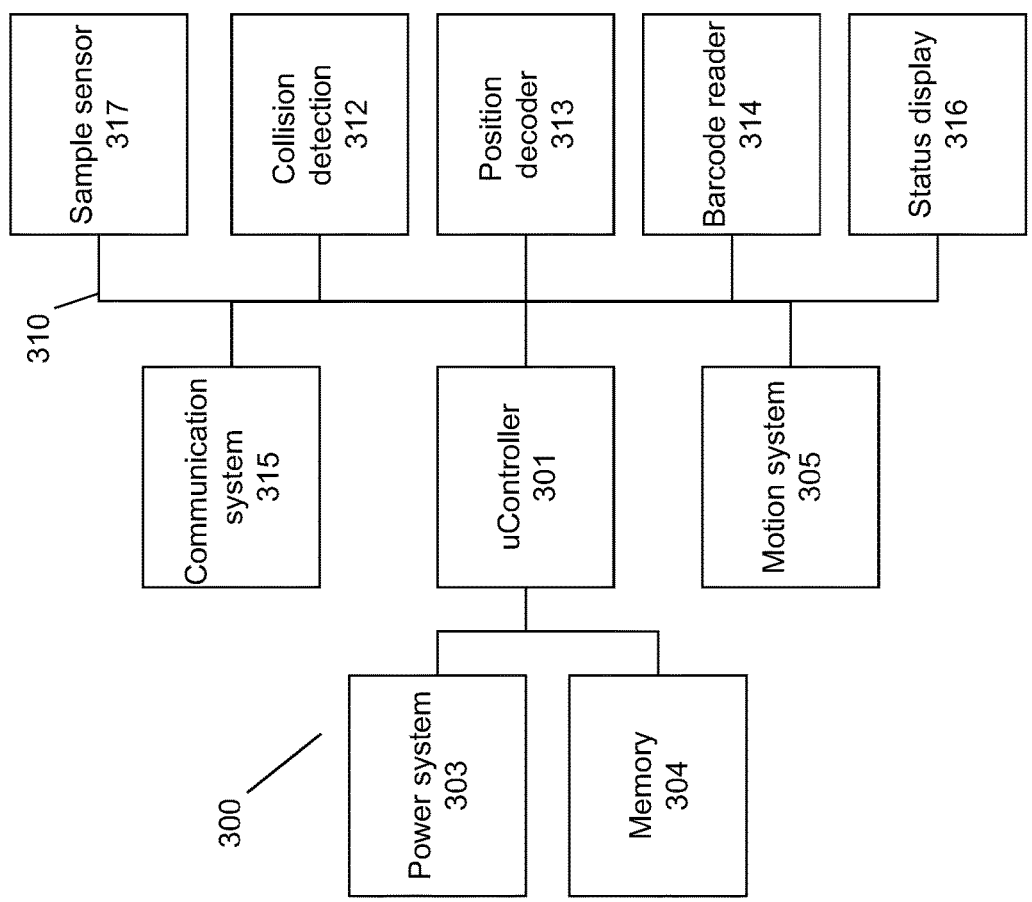
FIG. 5 is a system block diagram of control systems including onboard active carriers that can be used with certain embodiments disclosed herein.

FIG. 5 shows a top level system diagram of the control systems and sensors for an intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and use information to intelligently route around the track or convey status information to the track or other carriers.

Microcontroller 301 is responsible for operating the motion system 305, sensors 312, 313, and 314, and communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces. This can include requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, observe optical encoding in the track, and observe the instantaneous relative motion of the track. In some embodiments, position decoder 313 can also include inertial sensors, magnetic sensors, or other sensors sufficient to determine a carrier's current position, direction, velocity, acceleration, and/or jerk. In some embodiments, the components of the position decoder 313 can operate as part of the communication system. For example, in some embodiments, optical markings in the track can be electronically rewriteable, such as via an LCD or E-Ink display, and can be used by a central controller to convey routing instructions, along with position information. In these embodiments, image sensors used to determine position can also be used to receive the routing instructions or other data being communicated to the carrier.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication, or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing and Positioning

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

Because the carriers are actively involved in routing and trajectory control, the carriers should have a way to determine position and velocity information as they traverse the track, for example, of an IVD automation system. While accelerometers can provide acceleration information that can be integrated to determine a relative velocity and position, the precision of this information may be insufficient to be reliable for positioning carriers, and the samples they carry, at certain points in the system. For example, a pipette may need to be accurately placed in a tube on the carrier without contacting the walls of the tube. Therefore, it may be desirable to accurately position a carrier and its payload within about a millimeter at certain points on the track. In other sections of the track, such as straightaways, precise absolute position encoding may not be necessary.

In some embodiments, optical encoding on the track (e.g., on or in one or more track surfaces) can be used to provide position and/or velocity information to the carrier. Because the need for precision in the positioning information can vary throughout the system, some embodiments forego unnecessary encoding precision in portions of the automation system. In some embodiments, the natural surface characteristics in the track itself can be used for positioning encoding. This may allow an imaging device on the carrier to track the relative motion of the track surface as the carrier moves in areas where precise absolute positioning is unnecessary, such as straightaways or track sections between decision points. This natural encoding can be supplemented by placing synchronization marks at known intervals throughout the track. For example, in an area where coarse trajectory information is acceptable, natural pitting and other texture of the surface can be used for navigating between two absolute position marks (such as marks placed at a pipette or a decision point). Meanwhile, marks distinguishable from the surface texture can be placed at regular intervals, such as every 10 cm, to provide synchronization information and correct any error that may accumulate from observing the relative motion of the track surface.

Using position and/or velocity information obtained through observing the track (and any encoding), each carrier can follow routing instructions to reach destinations in the track system quickly, accurately, and without damaging or spilling samples being carried thereon. This position information can be used with information about the topography of the track and physical properties of the carrier's payload to determine the appropriate acceleration and velocity at any moment to minimize lateral forces on curves or allow the carrier to brake with sufficient distance to stop at intended destinations. In addition to position information, the carrier can make trajectory decisions with the assistance of onboard sensors (such as gyroscopes or accelerometers), or external information received by the carrier (such as information about the position and trajectory of nearby carriers). For example, accelerometers and track encoding information can be used to determine the current velocity, acceleration, and jerk, as well as the current position of a carrier. This information can be used by each carrier to determine its trajectory. In some embodiments, each carrier can convey this information to the system controller or other carriers.

Figure 6:
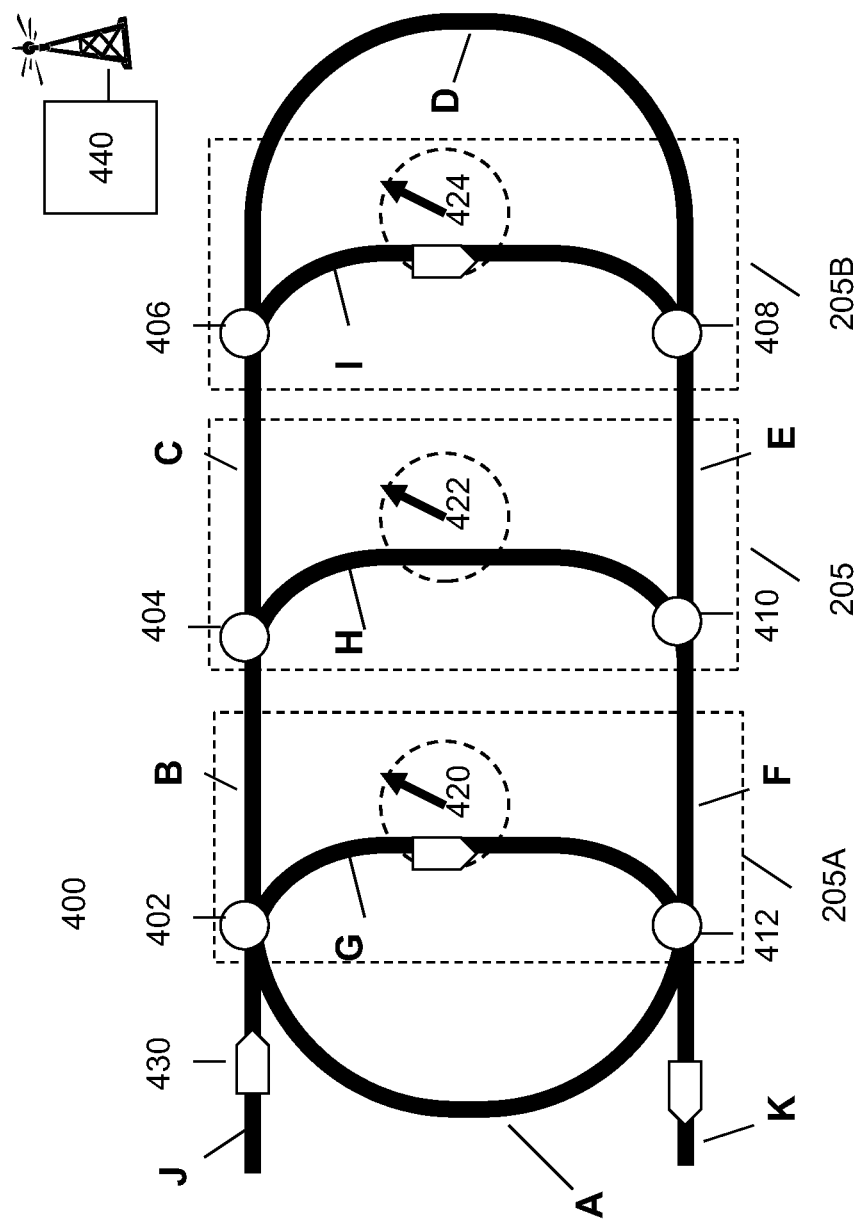
FIG. 6 is a diagrammatic view of exemplary routes in an exemplary track configuration that can be used for navigation of sample carriers in certain embodiments.

FIG. 6 shows an exemplary routing scenario in automation track system 400. Carrier 430 receives routing instructions from central management controller 440 via RF signaling. Carrier 430 can be any suitable embodiment of a carrier, such as carrier 300, shown in FIG. 5. Central management processor 440 can be a microprocessor, software operating on one or more processors, or other conventional computer means suitable for calculating the schedule for multiple carriers within the track system 400. Central management processor 440 can receive position information from multiple carriers, as well as any sensor information from sensors in the track 400 and/or information reported by the carriers. Central management processor 440 uses the status information of the carriers and track as well as the identity of samples carried by the carriers and the required assays to be performed by the system on these samples.

The exemplary track 400 shown in FIG. 6 includes a first curve segment A that connects to straight segment B and a pullout segment G, (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling stations 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 to a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting the onboard memory of the last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

Optical Navigation and Communication

In the exemplary embodiment shown in FIG. 6, near-field communication (e.g., RFID) can be used to convey the current track section, such as sections A-K, to a carrier 430 when it enters that section by placing RFID tags at the entrance to a track section. Information, including, for example, identification of the track section can also be conveyed via optical marks. These optical marks can act like signposts, identifying the track section the carrier is entering. These marks can also convey an absolute position (e.g., the precise starting point of the track section or any known position within the track system, such as a decision point or pipette location). The marks may also be dynamic, allowing carriers to receive information or instructions via optical markings. In some embodiments, within each track section, optical position encoding can be used to convey the relative position of the carrier within that track section or convey velocity of a carrier as it passes marks. This optical encoding scheme can be like a barcode that includes alternating light and dark lines (e.g., a series of marks) to convey bits of information. In some embodiments, the marks are generally periodically spaced in local sections. The distance between these marks can be referred to as pitch. The pitch is observed as a frequency by the carrier, as the velocity of the carrier creates a periodic signal at any photo-detector observing the marks.

Marks can include static or dynamic marks, or any combination of the two. For example, in a given configuration, a certain location of the track section may be an important absolute position. However, in other configurations, or for certain carriers, the position may not have importance. In those instances, an active mark can be rewritten and/or turned off. Static marks can be applied cost effectively (e.g., relatively inexpensively) to the track by any conventional means including, for example, using stickers, painting, etching, etc. marks onto the track surface to provide a static mark. Dynamic and static marks may also be active elements including, for example, E-ink, LCDs, LEDs, etc. placed in the surface of the track to provide reference points, and allow some ability to change the markings dynamically. Dynamic and static marks can also be created using a front or rear projection display to display marks to a carrier on or through a track surface using a laser or image projector.

In some embodiments, marks are provided by a rewriteable surface, such as a series of E-ink, LCD, or OLED panel displays. This may allow a central controller to update the marks dynamically or, as part of a configuration scheme, to convey dynamic content to the carriers, such as individualized routing instructions, or as part of a system configuration scheme. For example, a position within an analyzer may have significance when the analyzer is in a certain mode or configuration, such as a test mode.

In some embodiments, marks may not be black and white or other well defined two-toned combinations. For example, in some embodiments, the size of the mark varies along the track. The size of the mark can be used to convey information, such as using certain distinct marks for absolute position information, while using smaller marks repeatedly (e.g., every 10 cm or other suitable distance), to synchronize positions between absolute position marks. By using synchronization marks, the encoding scheme can ensure that carriers do not accumulate errors when observing the relative motion of the track surface between absolute position marks. Absolute position marks can be of any suitable size relative to the size of the carrier and carrier optics. In some embodiments, each mark is sized by the carrier to be visible within a single frame. In some embodiments, each mark is less than 1 cm.

In other embodiments, marks can be of multiple colors. The color of marks can convey certain information, such as the synchronization pitch of the encoding or the current track section. For example, black and white marks may be used in areas where high precision is needed, such as around pipettes, while red and white marks may be used on track sections that are near decision points or curves to indicate to a carrier that it should slow down. That is, the color can act as a warning. Similarly, encoding after obstacles such as decision points may be colored green to convey to carriers that it is an appropriate area to accelerate. In other embodiments, black and white marks may be of a certain known pitch while red and white marks are of a rougher pitch. Marks can be also reflective or made to absorb light on an otherwise reflective surface.

In addition to black and white marks (or any other contrasting color combination), a track 400 can convey position information via other artifacts. For example, the track can include landmarks, such as LEDs, or optical symbols that stand out from the track surface. Landmarks can indicate important features in the track, such as a stopping point for a test station, a braking zone entering a curve, or a braking zone approaching a decision point. Landmarks can be a type of absolute position mark.

In this example, there are two types of important landmarks. The first landmark may include the destination of the carrier. The carrier can determine if it is nearing its destination based on track encoding or a landmark feature, such as an LED, and uses this information to begin stopping or complete a stopping procedure. For example, a carrier may be instructed to stop at a precise location accessible to a pipette. This precise location may include an LED in the wall or floor of the track to assist a carrier in the stopping at a precise location with millimeter accuracy. In some embodiments, a carrier observes the track surface (e.g., surface texture and synchronization marks) to calculate rough trajectories, sufficient to move the carrier in a rough location of its destination. An absolute position mark can provide precise encoding to locate an exact destination.

Another available landmark could indicate a decision point. Using warning LEDs or marks as encoding in the track can convey the position of an upcoming decision point to a carrier relative to the carrier's current location. LEDs can provide dynamic encoded information. For example, a central scheduler may illuminate an LED at a braking position on the track some distance before a decision point. This can alert the carrier to decelerate to prevent unnecessary acceleration or collision. In some embodiments, if the carrier is not scheduled to turn at a decision point, the central scheduler can refrain from illuminating an LED. A carrier that does not need the landmark can simply ignore the landmark. Braking landmarks can serve as a failsafe to rectify a carrier's trajectory before turning. If the carrier will be turning and it observes a landmark that it did not expect, it can indicate that the extrapolated location perceived by the carrier is false. It may be necessary to update the trajectory to begin decelerating so that the velocity of the carrier is slow enough when it turns at the decision point to prevent unnecessary lateral forces that could harm or spill a sample.

Conveying Data, Position, and Trajectory Information Using Marks

Static and dynamic marks can include marks spaced along a track surface providing marks of variable pitch to regulate the acceleration or velocity of each carrier. For example, a central controller can convey to a first carrier one pitch of encoding marks and another pitch of encoding marks to a second carrier. In this exemplary embodiment, a wider pitch can be used with a carrier that a central controller has deemed capable of higher speed on the track section. By using a wider pitch, a carrier observing the frequency of the marks can be led to believe that it is traveling slower than if the marks being displayed with a finer pitch. For example, a wider pitch can be used for an empty carrier. Meanwhile, a finer pitch can be displayed to a carrier that has a full payload or that a central controller knows will be turning soon. In these embodiments, the position encoding information can be used to convey distance and suggested velocity information to the carrier, or can display or just convey velocity information. In some embodiments, dynamic marks can be used to dynamically adjust the pitch to control the speed and/or acceleration profile of individual carriers separately as they traverse each track section. This may allow individualized control of each carrier in substantially real time, without requiring direct, centralized control of the motion systems of the carriers. Marks in the track can allow a central controller to issue general trajectory instructions, much like an aircraft controller, which will be interpreted by the carrier. Meanwhile, certain parts of the track may include static marks to control trajectories of carriers based on a track configuration, much like static road signs seen on highways.

Velocity and/or position information can be conveyed via one or more repeating series of alternating lines. These marks can be used by the carrier, much like a clock signal. By knowing the distance between two marks, the carrier can count the marks to determine its relative distance within the track section. The carrier can also determine its velocity within the track section by observing the frequency of these bands. By using binary optical marks, the carrier can read the encoding using simple optical means, such as one or more photodiodes. This can reduce the cost of components of the carrier while still providing reliable position information.

In some embodiments, more than one row of encoding marks can be used. The multiple rows of bands can convey multi-bit information and can convey direction or the pitch of the encoded marks. It will be appreciated that more information can be conveyed using more rows. Multiple rows can be read via a plurality of photo-detectors or a low-resolution camera. The photodetector can also include a lighting source to assist in viewing the marks, like a barcode reader.

In some embodiments, one or more rows of marks can be used and the pitch of these marks can be modulated to convey information, including identification of the track section, direction, absolute distance, or warnings, such as a decision point, such as 402, 404, 406, 408, 410, or 412, or a curve (such as track section D) is approaching. In this manner, each row can be considered an information channel. If a row utilizes an active display that can be actively updated, the row can convey information in a dynamic data channel that is tailored to the carrier receiving it.

In some embodiments, variable pitch encoding can be used to convey data, such as routing instruction, trajectory instructions, configuration information, or any other information that the automation system may want to convey to a carrier. This method of conveying information can have the advantage that it may reduce or eliminate the cost of wireless transponders within each carrier for communicating with the automation system. This may reduce the energy usage of each carrier, allowing carriers to be smaller and have smaller battery requirements. Furthermore, optical communication may provide a more secure form of communication that reduces or eliminates problems due to electromagnetic interference and eavesdropping, allowing some information to be conveyed without need for encryption.

Figure 7C:
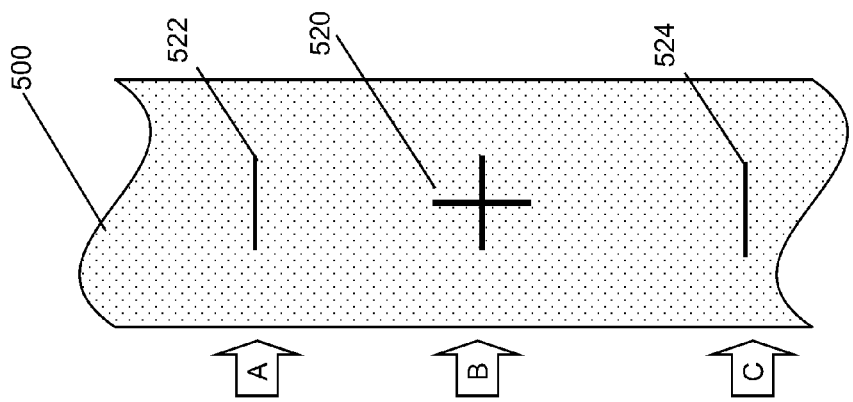
FIGS. 7B-7D are surface views of markings on exemplary track sections for use with some embodiments.
Figure 7B:
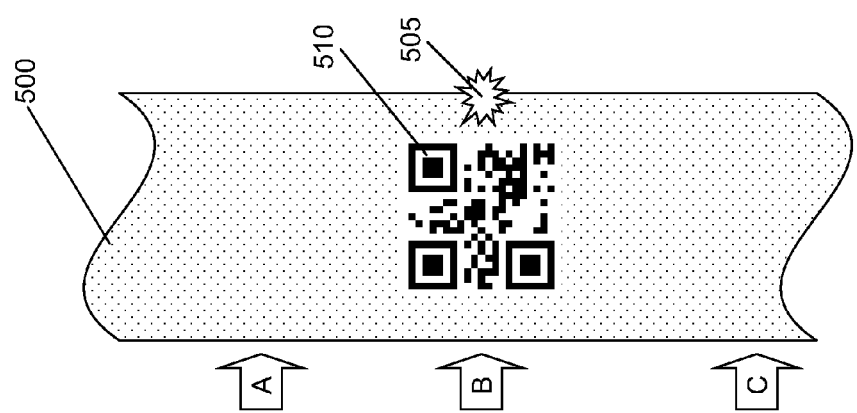
Figure 7A:
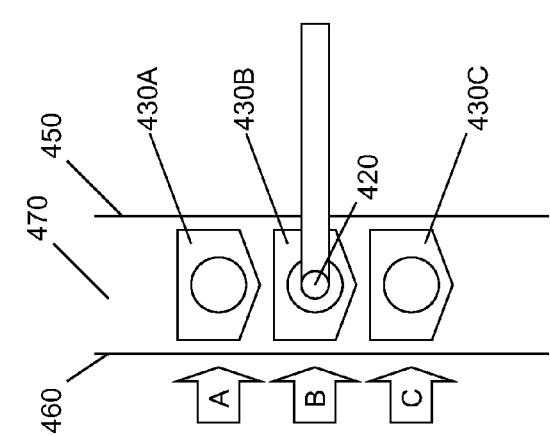
FIG. 7A is a top view of an exemplary track section for use with embodiments of an encoding scheme.

FIG. 7A illustrates different positions at which a carrier 430 can stop. In this example, pipette 420 operates a small sample queue. Motion of the carriers in the queue can be constrained by surfaces 450, 460, and 470. Here, carrier 430A stops before pipette 420 at position A. Meanwhile, carrier 430B stops at position B directly under pipette 420. This allows pipette 420 to interact with the sample carried by carrier 430B. Carrier 430B may be required to stop within a precise location with respect to position B to allow pipette 420 to accurately interact with the sample. For example, a precise location may include locating carrier 430B within a millimeter of position B. In other embodiments, more precise positioning may be provided, for example, in one embodiment within 0.5 mm; and, for example, in another embodiment within 0.1 mm. If the local queue is random access, another carrier 430C may be positioned at position C while it waits to interact with pipette 420 at position A or B. The exemplary station shown in FIG. 7A may include testing station 205A (see FIG. 6), but similar examples may exist at the stations served by pipettes 422 and 424.

To achieve precise position encoding around pipette 420, the marks shown in FIG. 7B or 7C may be used. In the example shown in FIG. 7B, two types of absolute position marks are used. QR code 510 is placed on track surface 500 to provide a precise location for position B. It should be noted that QR codes inherently have precise positioning information within the structure of the mark. For example, the large square features of QR code 510 provide reference positions within the mark itself, as well as providing orientation information. Similarly, in some embodiments, a light source, such as LED 505, can also be provided at position B to add further or alternative precision. In other embodiments, no LED is used as the QR code 510 provides sufficient absolute positioning information. Marks 510 and 505 need not be on the same track surface (but can be in some embodiments). For example, one could be on the floor of the track, while one may be on the wall track. In this example, positions A and C are any known distance from position B, and a carrier 430 can utilize the natural surface texture of track surface 500 to observe the relative motion of the carrier over the track surface to move a short distance between position B and position A with relative precision, as explained below.

FIG. 7C shows an alternate example of position marks sufficient to indicate positions A, B, and C. As shown in FIG. 7C, an absolute position mark 520 can be placed on surface 500. In this example, absolute position mark 520 is a two-dimensional radical style mark. This can be used to provide longitudinal and lateral position information to carrier 430. For example, in an embodiment where a carrier has freedom of movement along the track as well as transversely to the track, this two-dimensional information can be quite useful. For example, embodiments where a carrier has its own steering mechanism and is not necessarily physically guided by track walls, a carrier's lateral position may vary by a few millimeters or centimeters along the length of track. Lateral positioning information can then be used to correct its trajectory or to convey the deviation in the lateral placement of a sample to a sample pipette so that a lateral adjustment can be made by the pipette when interacting with the sample.

Between absolute position marks, track surface 500 can include relative position markers, such as synchronization marks. Marks 522 and 524 shown in FIG. 7C are examples of synchronization marks. In one exemplary embodiment, synchronization marks may be placed along a track at predetermined intervals, e.g., every 10 cm. In such an embodiment, positions A and C would correspond to synchronization marks 522 and 524, respectively, of FIG. 7C, where position A is 10 cm away from position B, for example. In contrast to the exemplary embodiment shown in FIG. 7B, synchronization marks 522 and 524 can also act as absolute position marks at position A and position C, respectively, such that a carrier need not rely on precision in its observation of relative movement of the track to correctly position itself at position A or position C. It should be appreciated that the exemplary embodiment in FIG. 7B may also include synchronization marks, which may or may not be at positions A and C.

Figure 7D:
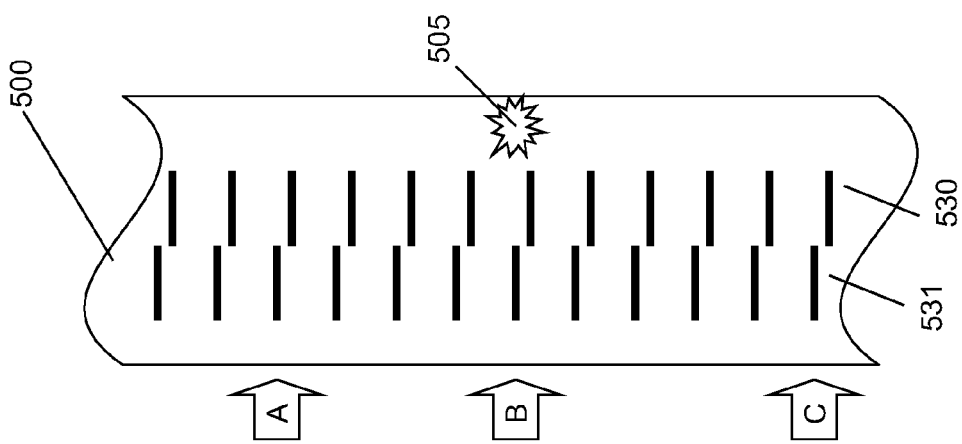

In some embodiments, the marks shown in FIG. 7D may be used to achieve precise position encoding around pipette. Encoding 500 can be placed or attached onto the left side wall 460, the right side wall 450, or the bottom surface 470 (see FIG. 7A). In this exemplary embodiment, encoding 500 includes one or more parallel rows of regularly repeating marks 530 and 531. In this example, marks 530 and 531 share the same pitch, but are phased shifted relative to one another. When shifted asymmetrically, as shown in FIG. 7D, the marks can convey direction. Observing both rows 530 and 531 will indicate the direction the carrier is traveling. For example, when traveling backwards (towards the top of the figure) the marks in row 530 will appear to precede those in row 531. When traveling forward (towards the bottom of the figure). The marks in row 531 will appear to be ahead of those in row 530. The orientation of the encoding in FIG. 7D is arbitrary for illustration. For example, if etched on a vertical surface, row 531 may be a bottom row, while row 530 is a top row.

In some embodiments, only a single row of marks need be used to give both position and direction. If the carrier is equipped with two adjacent photodetectors spaced relative to one another at a distance that is not a multiple of the pitch of the marks (such as spaced closer than adjacent marks), observing pulses in both photodetectors will reveal the direction the carrier is traveling. For example, when traveling forward the fore photodetector will observe a mark before the aft photodetector. In some embodiments, a laser is used to illuminate the encoding resulting in a speckle pattern, like that observed in an optical mouse. This allows the carrier to determine direction and velocity information easily with a single row of position encoding.

In some embodiments, an LED 505 can illuminate at a predetermined position, such as position B to indicate the ideal location for stopping to interact with pipette 420. In some embodiments, pipette 420 can move to multiple positions, including positions A and C. In these embodiments, additional LEDs can be placed at those locations and illuminate when a carrier is required to stop at those positions. If the carrier is not supposed to stop at a position, the LED can be turned off (or not illuminated) so that the carrier will not see the landmark.

In some embodiments, marks 510, 520, 530, and 531 can be dynamic marks, being electronically rewriteable for each carrier or static. This may allow carriers to be directed to different stopping locations and to receive different information from the optical marks along the track. The type of information that may be displayed to various carriers, both statically and dynamically, is discussed throughout. It should be appreciated that any of the types of marks disclosed herein may be static or dynamic (or any combination thereof), as appropriate to the application.

Figure 8A:
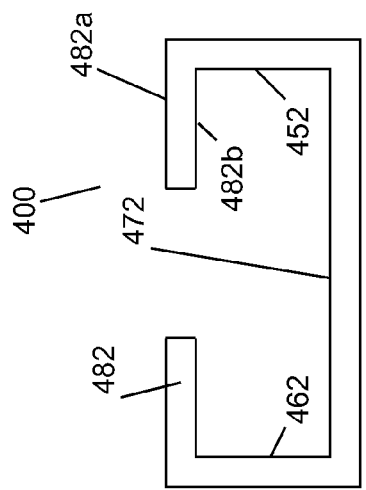
FIGS. 8A and 8B are cross-sectional views of exemplary tracks used with embodiments of an encoding scheme.
Figure 8B:
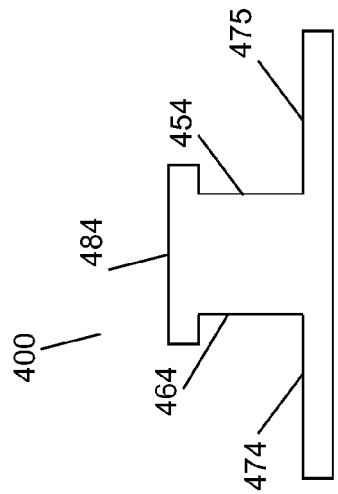

FIGS. 8A and 8B show cross-sections of exemplary tracks 400 that can be used with the present invention. These cross-sections have multiple surfaces that can be used for encoding position information. For example, FIG. 8A shows a trough-like track having a bottom surface 472, a right surface 452, a left surface 462, and at least one top surface 482, top surface 482 also having an upper surface 482a and lower surface 482b. Any of these surfaces may be chosen for encoding position marks. A suitable carrier that travels on this track can then include photodetectors or other optical detectors positioned to observe the marks. The track in FIG. 8B is a monorail-type structure. This track has respective right and left bottom surfaces 475 and 474, respective right and left vertical faces 454 and 464, and at least one top surface 484. Similarly, any of these surfaces can be chosen as appropriate for encoding position information.

Position marks can be applied to any of these surfaces in any suitable manner. In some embodiments, this can include applying a sticker or label, etching, painting, marking, changing a reflective property, applying an electronically rewritable surface to the track, projecting marks with a projector or laser source, or by any other suitable means.

FIGS. 9A-9D show alternate embodiments for encoding arbitrary information and position information by using one or more rows of encoded marks in the track. In the example shown in FIG. 9A, there are three rows/channels of encoded information. Rows 512 and 532 include regularly spaced marks that reveal position and direction information. As explained above, a single row can be substituted for these two rows if the carrier has suitably configured photodetectors to allow detection of direction. Row 550 includes irregularly spaced marks, which can be periodically repeated. These irregularly spaced marks can be called characters. The characters in row 550 can be used to convey information such as the track encoding pitch, the current track section, absolute position information, or any other suitable information. Because row 550 is used with regularly spaced rows 512 and 532, the information in row 550 can be used for coarse absolute positioning information or other data while rows 512 and or 532 can be used for accurate local positioning based on counting. In some embodiments row 550 can be considered a data channel while row 512 and/or 532 can be considered a clock channel.

In this example, row 550 has synchronization information in marks 570. In this example, two closely spaced marks can be a special character used to synchronize data or synchronize positioning counts as explained throughout.

FIG. 9B shows an alternate encoding. Here, position or data frame synchronization characters 572 can be placed in row 532A. The carrier can observe the gaps in the otherwise regularly spaced pattern and use this information to synchronize with the track encoding. Meanwhile, row 550A can be more efficient as a data channel unburdened by frame synchronization characters.

FIG. 9C shows yet another embodiment of position and data encoding. In this embodiment, only one regularly spaced row 512 is used. Meanwhile, data channel 550 can be used for pitch, rough absolute position encoding, or other data. In this embodiment, the carrier may determine its direction, for example, via an accelerometer, observing the direction of the travel of row 512 using more than one photodetector, or other suitable means. In the embodiment shown in FIG. 9C, the left-hand marks 512 may act as a clock signal for data in row 550. It will be appreciated by one of ordinary skill in the art that any known encoding scheme used for electrical signals may also be adaptable for use in these encoding schemes. For example, a two row encoding scheme, such as FIG. 9C could use an encoding scheme similar to a visual version of an I2C bus.

In some embodiments, the marks can be changed dynamically, such as including at least one row of marks 550 that includes LCD or E-ink displays to send information optically to the carrier. In these embodiments, it may not be necessary for a central controller to communicate wirelessly with a carrier as row 550 could act as a low bandwidth data channel to convey dynamic information to a carrier. For example, data row 550 can be used to convey updated routing information to a carrier as it traverses the track. In some embodiments, there can be multiple channels of data 550.

It should be noted, that the cost to add information in the encoding on the track can be relatively low, particularly where no dynamic information is encoded, because those encoding channels/rows can be painted or etched. The only substantial costs associated with adding multiple rows may be caused by the increased cost of the hardware used by a carrier to read multiple rows or channels. It should also be noted that all rows do not need to share a single surface as multiple surfaces may be available as illustrated in FIGS. 8A and 8B.

Figure 9D:
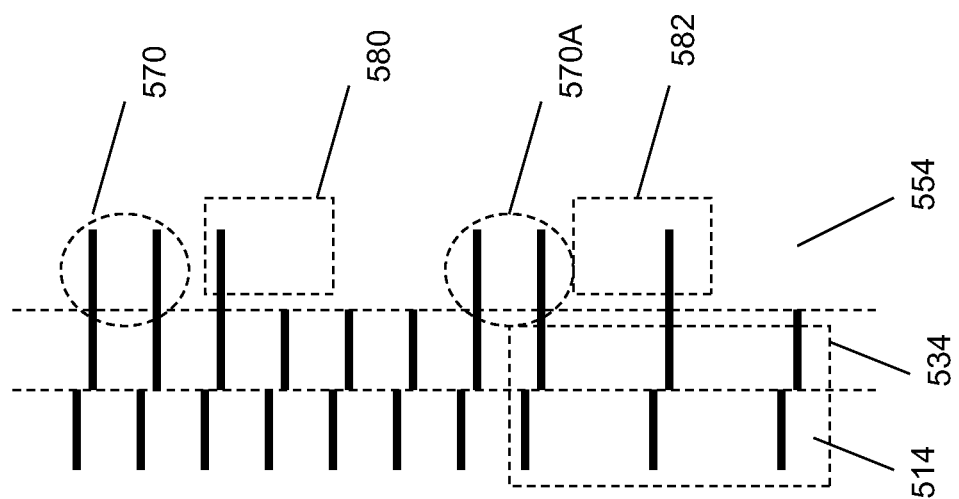

FIG. 9D illustrates an embodiment where the data channel 554 can be used to identify the local pitch of regularly spaced rows 514 and 534 or other local information. In this example, (when a carrier travels down the page) synchronization character 570 can be used to determine that data character 580 is one position away, indicating a first pitch. Subsequent frame synchronization character 570A can be used to determine the data character 582 is one position away. This can indicate a second pitch, which in this example is a wider pitch in channels 534 and 514. It should be noted that any of the other frame synchronization techniques described can be used. Similarly, some embodiments may include only a single regularly pitched encoding channel.

FIGS. 10A-10D show encoding schemes where the rows of pitched marks can be used to encode synchronization marks or even data. For example, FIG. 10A illustrates two regularly pitched rows 516 and 536, where the absence of the mark in row 536 acts as a synchronization character 576. In FIG. 10B, regularly pitched channels 517 and 537 include synchronization and data. The absence of two marks at position 577 can indicate a synchronization of a position count, as well as a single bit of data (or fraction thereof in embodiments where error coding is used). This data can be used to identify the pitch, track ID, or any other appropriate information, such as routing information. As shown in FIG. 10C, the left-hand row 518 can have an absent character 578 to indicate synchronization information while the right-hand row 538 includes regularly pitched marks. As shown in FIG. 10D, a single row of marks 518A can also be used to include both synchronization marks 578A, and position marks at otherwise regular intervals. In these embodiments, the carrier can use the techniques described herein to determine direction without requiring a second encoded row. In some embodiments, missing marks 578A can also be used to convey low-bandwidth data. For example, the presence or absence of every 10th mark can convey data, such as track pitch or track section ID.

Figure 11C:
FIGS. 11A-11C are surface views of markings on exemplary track sections for use with embodiments of an encoding scheme.
Figure 11B:
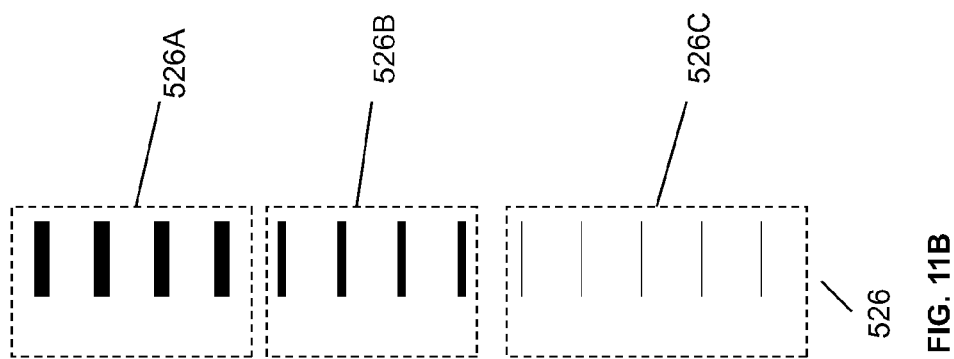
Figure 11A:
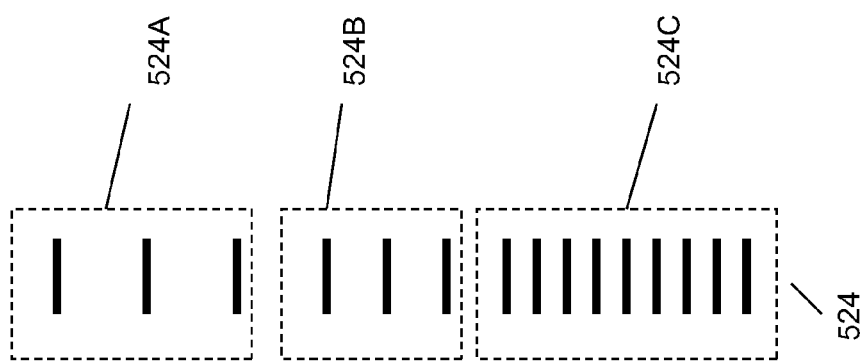

FIG. 11A shows an embodiment, where a variable pitch encoding can be used without an optical indicator of pitch. This embodiment encoded row 524 includes multiple sections of regularly spaced marks 524A, 524B, and 524C, which are all encoded with different pitches. Pitch information can be conveyed through near field communication to a receiver in the carrier or through optical means, such as the encoding itself. In some embodiments, no pitch information is conveyed to the carrier. Instead, the pitch is chosen based on the conditions of the track, such as a straight away or curve. This can convey the predetermined ideal maximum speed through a section of the track based on curvature or conditions. Wider pitch 524A may be used on a faster section of track (e.g., a straight away), medium pitch 524B a slower sections (e.g., a curve), while finer pitch 524C can be used at destinations (e.g., a work station). A carrier observing the frequency of the marks relative to its own internal clock will see the same frequency in sections 524A and 524C if an appropriate faster speed is used in section 524A, and a slower speed is used in section 524C.

Speed may also be regulated without conveying the pitch to the carrier. A carrier can be configured to traverse a track at a maximum rate defined in marks per second. When traversing a finer pitch pattern, a processor on the carrier can apply the pitch speed limit to inherently slow the carrier down to limit the rate at which the carrier passes marks. In track sections where the pitch is wider, a processor on a carrier will inherently cause the carrier to speed up to increase the number of marks observed per second to reach the mark speed limit. It should be appreciated that this effect can be used to utilize dynamic marks to control the trajectory of a carrier without the need for other communication. When a central controller wants a carrier to speed up, the increased speed limit can be conveyed optically to the carrier, such as by widening the pitch of marks on the track near the carrier. In this manner, optical marks can act as speed limit signs, and dynamic marks can act as dynamic speed limit signs.

These variable pitch marks may also be used for distance acquisition. Each carrier can have an internal reference for the "distance" of a track section listed not by physical distance, but by marks in the track. For example, a short track section with fine pitch, such as near a pipette, can have a large distance when measured in marks, such as 500 (e.g., a 50 cm section with 1 mm pitch). Meanwhile, a longer section of high speed track, such as a straight away, can have a few number of marks with a low pitch count, such as 15 (e.g., a 150 cm track section with a pitch of 10 cm). In some embodiments, the pitch can be chosen to act as a speed throttle for the carriers, which can make trajectory decisions easy and reduce computation requirements to reduce the cost of producing carriers.

FIG. 11B shows an embodiment where a single row of marks 526 is encoded with regularly spaced marks, but where marks are different widths. This can allow a single row of optical encoding positioning information to convey both a clock signal in the pitch, as well as other information/data in the observed pulse width. For example, section 526A may convey a faster section of track, section 526B may convey a medium speed section of track, while section 526C may convey a slow section of track. In some embodiments, the width of a mark can also be used to convey the current pitch being used or other data. The width of the marks can be called a duty cycle or pulse width of the marks, as the perceived relative time a sensor detects light or dark areas will change based on the width, even though the frequency/pitch does not change. The marks can thereby be used to convey information via pulse width modulation.

FIG. 11C shows an embodiment similar to that shown in FIG. 11B. In this embodiment, encoded row 528 encodes a data channel with the bit rate substantially near the pitch of the encoding. (It should be noted that error coding schemes can also be used such that each apparent bit is a fraction of a bit, allowing for larger hamming distances in the signal.) In this embodiment, a special synchronization character 579 can include two regularly spaced marks that overlap, while all other marks are regularly spaced, but have varying widths to convey data. In this regard, the embodiment shown in row 528 is much like a continuous barcode. Synchronization mark 579 may be regularly placed throughout the encoded track and act to synchronize data frames and/or velocity and position.

It will be appreciated that any suitable encoding scheme can be used to convey data along with positioning information. For example, regularly spaced marks can have a width that is chosen based on a Manchester-based encoding. Manchester encoding allows both synchronization information in regularly spaced marks as well as data in the character of those marks. It will be appreciated that many encoding schemes used in the wireless space that encode both data and clock information in a single signal can be used in the optical encoding scheme of the present invention. This can allow static or dynamic (if marks are rewritable) delivery of data as well as precise positioning based on the pitch of the marks.

It will be appreciated that any of the encoding schemes shown in FIGS. 11A-11C can be encoded dynamically with an active display, such as an LCD or e-ink display. In some embodiments, the marks used by any of these encoding schemes can include illuminated surfaces such as LEDs to create the marks or spaces between marks to increase the readability of the encoding. These LEDs can also be dynamic. In some embodiments, dynamic optical encoding can be used to convey enough data and instructions to a carrier that RF communication (and related components and expense) may not be necessary. Similarly, carriers may be able to receive routing instruction in just-in-time fashion, as explained below, lowering requirements for processing and memory onboard carriers, further reducing expense and power requirements.

It should also be appreciated that the precision by which carriers determine their position can be greater (or less) than the pitch of the marks. For example, sub-pitch position accuracy may be achievable by using two analog (or at least multi-state) photodetectors spaced closely apart. When these two photodetectors observe the same mark, the precise location of the carrier relative to that mark can be determined by comparing the relative intensity of the mark observed by both the photodetectors. For example, if two photodetectors are positioned to partially observe the same mark, the photodetector with the stronger signal is determined to be proportionally closer to the mark. This relative observation can be used to achieve sub millimeter accuracy even when the pitch of the marks encoded in the track is greater than a millimeter.

Figure 12:
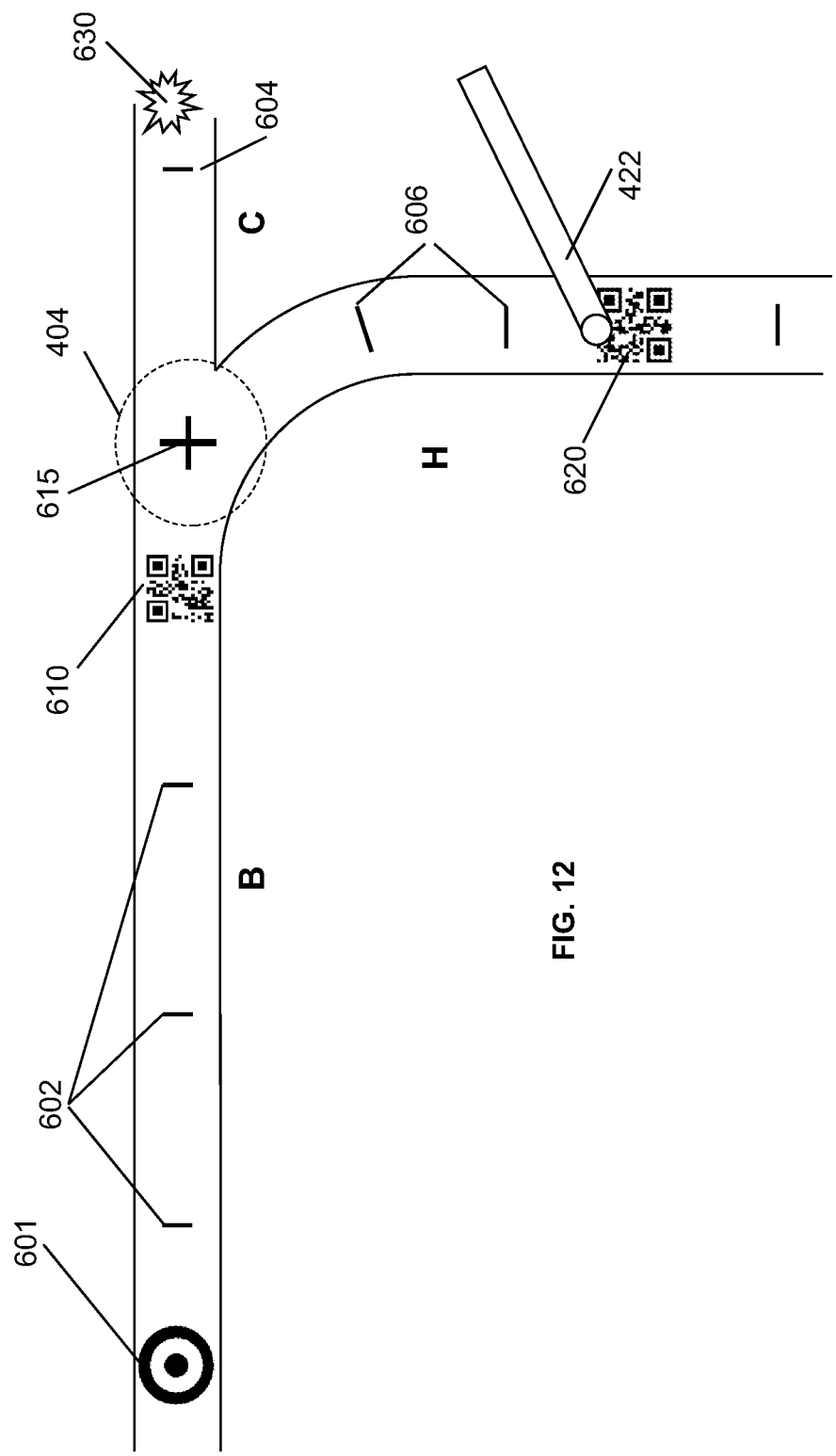
FIG. 12 is a top view of exemplary track sections employing dynamic marks for routing carriers in certain embodiments.

In addition to rows of encoded marks, dynamic and static information can be conveyed using landmarks. FIG. 12 shows various examples of possible mark placement within a track system, such as that shown in FIG. 6. Each of these marks may be static or dynamic, as appropriate to the application. Upon entering section B in FIG. 12, a carrier may observe a reference mark 601, which may be a two-dimensional bulls-eye pattern. This can be used for two-dimensional reckoning of a carrier as it enters a track section to convey to the carrier that it has entered a new track section. Mark 601 may act as an absolute position mark. In some embodiments, after observing mark 601, a carrier can proceed by observing the relative motion of the track as it traverses the track. This can include observing the motion of shadows created from an off-axis light source using an imaging device and comparing successive frames to note the motion of features within the image. This can provide relative accuracy in estimating a current trajectory and for extrapolating a current position within track section B.

In some embodiments, synchronization marks 602 may be provided at regular intervals on the track surface of section B. In embodiments where relative motion is observed by the carrier between marks (e.g., by observing relative motion of natural variation in the track surface or by using an onboard accelerometer), by placing synchronization marks 602 at regular intervals, any drift in positional accuracy due to imprecision in the observation of the relative motion of the track as the carrier traverses can be corrected or accounted for. This error can be an accumulation of sampling error, such as due to frame rate and image inaccuracies (such as blurry images or a low-resolution), due to image processing errors (such as erroneous correlation of image artifacts) or rounding or precision errors in an accelerometer observation. By providing robustness against errors in observing relative motion of the carrier to the track surface (and/or correcting such errors), lower precision imaging sensors may be employed, which may reduce the cost of implementing the carriers. Furthermore, synchronization marks can provide additional positional accuracy at low cost, in some embodiments eliminating the need for sensors to observe position, velocity, and acceleration between landmarks/position marks and synchronization marks.

In the example shown in FIG. 12, prior to reaching a decision point 404, position mark 610 can provide information to a carrier about the upcoming decision point 404. Mark 610 may be an absolute position mark in the form of a two-dimensional data mark, such as a QR code, datamatrix, or Aztec code, for example. A QR code can include many bits of data within the binary patterning present in an image. The amount of information that can be conveyed by the QR code depends on the resolution of the binary information in the QR code. For example, a version 1 QR code provides a 21×21 pixel image, while a version 4 QR code includes a 33×33 pixel image, which can convey up to 50 characters of information with error correction. Any suitably sized QR version can be chosen and any known QR encoding scheme can be used, as suitable for the application. For example, a lower resolution QR code may be used to reduce the cost of the imaging sensors used in carriers if large amounts of information do not need to be conveyed in a single QR code. As more accurate imaging sensors become available (e.g., cheaper), denser QR codes may be easily used with some embodiments. QR codes can be advantageous for use with embodiments of the present invention because of the built-in error coding to provide robustness, while also including readily distinguishable features that provide positional and orientation reference points to a carrier (e.g., the fixed bulls-eye patterns in the corners of the QR code).

In this example, QR code 610 may be used for both position and to convey information about decision point 404 to the carrier with enough time for the carrier to navigate appropriately. For example, if a carrier is scheduled to turn, position mark 610 can be dynamic and rewritten to include an instruction to turn in the QR code information. Similarly, if a carrier is scheduled to go straight, a position mark 610 can be rewritten to include an instruction in the QR code information to proceed past decision point 404. An additional absolute position mark 615 may also be used at decision point 404 to indicate a precise location where a carrier needs to initiate a turn or otherwise interact with decision point 404. If the carrier proceeds onto track section C, it can observe the track surface to provide real-time trajectory information. Upon observing synchronizing position mark 604, the carrier may correct any accumulated error in its position or use the first synchronizing position mark 604 to synchronize the expected position of subsequent synchronization marks. Position mark 630 can be in the form of an LED to indicate an important location within section C, for example. Because mark 630 can be dynamically changed, it may only be illuminated when it conveys relevant information to a given carrier.

Alternatively, if a carrier diverts onto section H, at decision point 404, the carrier can also determine a real-time trajectory from observing the relative motion of the track surface and/or the carrier. Upon encountering marks 606, any error accumulated in that estimate of the real-time trajectory of the carrier can be corrected. Marks 606 can be dynamic and convey relevant position or velocity instructions to the carrier.

Proceeding along section H, when a carrier reaches a point at which it can interact with pipette 422, the carrier encounters another absolute position mark 620. Here, position mark 620 may be a static or dynamic QR code that includes data that identifies the position as relating to pipette 422 or provides instruction relating to the carrier at pipette 422. For example, the QR code may say "pipette 422" or "carrier 22 stop here." By providing additional information besides just a mark that indicates a seemingly arbitrary point on the track, the observing carrier can be guaranteed that it has reached the right absolute position within the track system by reading the QR code of its destination.

It should be appreciated that the various types of absolute position marks shown and described with reference to FIG. 12 may be dynamic or static to provide appropriate functionality. For example, a mark indicating a landmark, such as the interaction point for pipette 422 or the intersection point for decision point 404 may be static, as all carriers may use this information. Marks that convey routing instructions, speed instructions, turning instructions, or other data that is specific to a carrier can be dynamically displayed, using an electronically rewriteable display. In some embodiments, a combination of static and dynamic marks can be used, allowing rewriteable displays to only be used in certain sections of the automation track. This can reduce complexity and cost, as much of the track may be manufactured using cheaper materials with statically printed, etched, or embedded marks. For example, dynamic marks can be used at intersections, interaction points, or near decision points, while static marks can be used to regulate speed on track sections between these dynamic marks.

Figure 13:
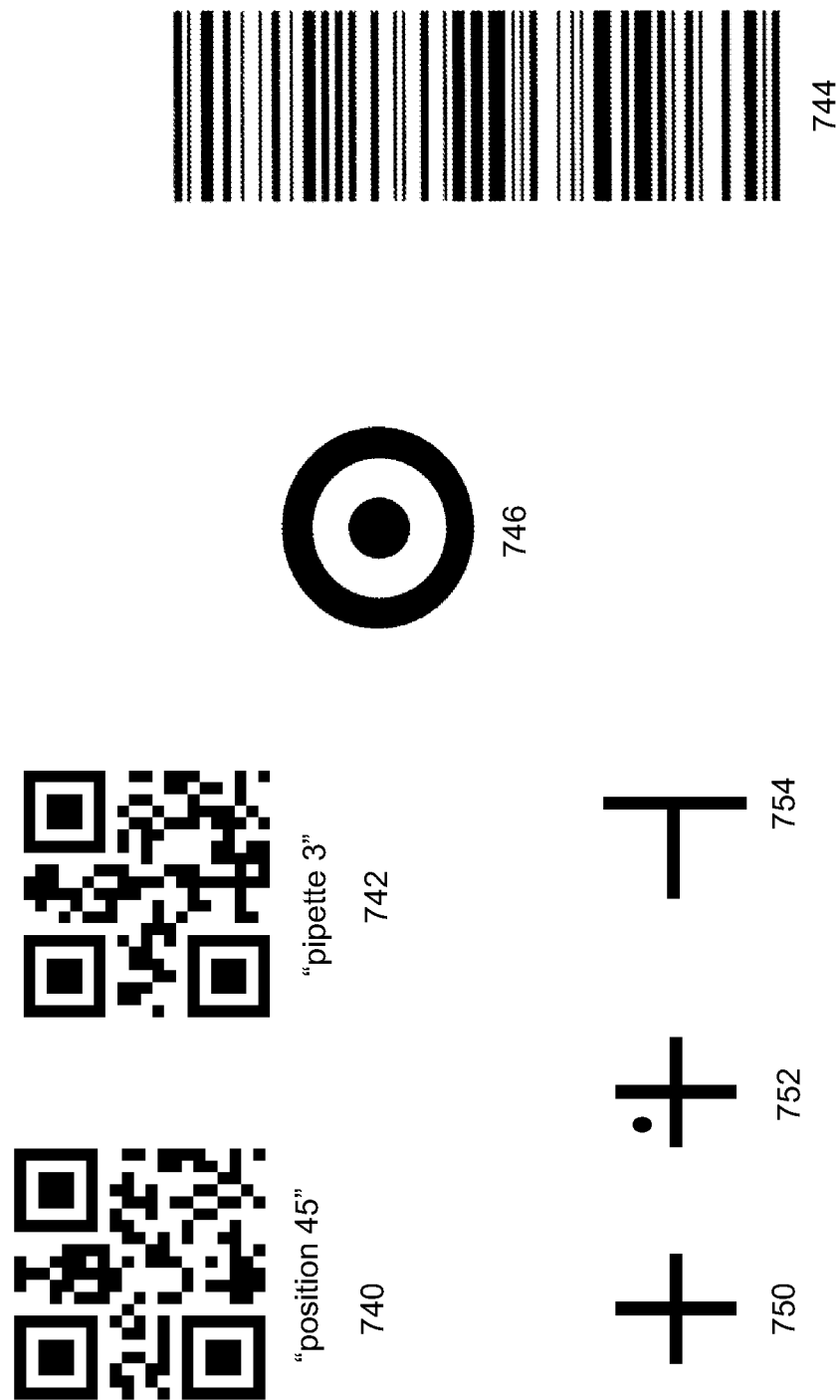
FIG. 13 is a depiction of exemplary types of position and data marks for use with certain embodiments.

FIG. 13 shows some examples of data and position marks that may be suitable for certain embodiments of the present invention. QR code 740 is a version 1 QR code including the phrase "position 45." This mark can be used to indicate an identification of a given absolute position (e.g., an absolute position mark) so that the identification of an absolute position, along with the location of an absolute position, can be conveyed to the carrier. QR code 742 is an informational mark containing the phrase "pipette 3." This exemplary mark can be used to convey a stopping position for interacting with a pipette, such as a position accessible to pipette 3, and can convey both the identification of the position and the precise location of the position or may be used to dynamically convey routing instructions to an individual carrier at destinations for carriers. Other QR codes can contain dynamic routing information or other information to be conveyed to a carrier. These may include "turn right at next intersection," "warning," "speed up," "go to position 45," or any other suitable instruction. In some embodiments, dynamic information may be used to configure the carrier, such as loading a map of the track for the carrier to use, instructing a carrier to use a certain acceleration profile based on the type of payload being carried (e.g., use a STAT sample profile, or a reagent waste profile), which may be used when interpreting how to accelerate and decelerate in relation to position or synchronization marks. In some embodiments, a carrier may have software (e.g., new firmware) loaded based on successive QR or other marks.

These marks may be suitable for electronically rewritable surfaces, where the content of the QR code can be dynamic, such that different carriers receive different messages within the absolute position mark formed by the QR code. For example, a first carrier can observe a QR code and a successive carrier can be shown a different QR code (or other mark suitable for conveying data) that identifies the current position and identifies a different next position for the carrier to navigate to. In some embodiments, dynamic data marks, such as QR codes may be updated while a carrier waits, viewing successive frames, allowing low resolution marks to convey larger amounts of information in a serial fashion. In some embodiments, multiple dynamic marks along the track can convey information to a moving carrier that contains more information than a single mark could.

Mark 744 is a barcode. A barcode works in substantially the same way as a QR code, but in one dimension. A barcode can use certain marks (e.g., a leading mark or a fixed bold mark within the code) within the overall barcode to indicate a one-dimensional absolute position. The barcode can also convey certain data, such as an identification of the position, by using the content of the barcode. A barcode may have further advantages over more complex marks, such as QR codes, because a barcode may be laid out along the path of motion of a carrier. This may allow simple optics, such as a single photo diode to receive large amounts of data in serial fashion as the carrier moves. In some embodiments, a substantial portion, such as several feet along the track, can contain electronically rewritable display segments that allow a large amount of information to be conveyed to a carrier as it traverses the display segments.

Position mark 746 is a bulls-eye mark, which is a symmetric two-dimensional mark suitable for indicating an absolute position in two dimensions, but may not be suitable for conveying other information. Position mark 750 is a cross. Like the bulls-eye, the cross is symmetric, and conveys little orientation information or data. Marks 752 and 754 are examples of simple position marks that convey position and orientation due to asymmetry but, unlike QR codes or barcodes, can only convey a limited amount of other data (e.g., one to three bits), if any. These simpler marks may be suitable for embodiments where a carrier has other means for receiving information, such as near-field/RF communication or a wireless antenna. Simpler marks may be advantageous in that they may allow a carrier to employ simpler optics and image processing, which may be cheaper.

These simpler marks may also be suitable for use with embodiments where carriers react to individual localized instructions from a local track section. For example, marks 750, 752, and 754 may be useful for conveying trajectory instructions. Mark 750 may inform a carrier that it should stop at that location. Mark 752 may tell the carrier to slow down in preparation for a left turn. Mark 754 may tell the carrier that it should turn left. Each of these marks may be dynamic, and change based on the individual routing instructions needed for each carrier.

Figure 14:
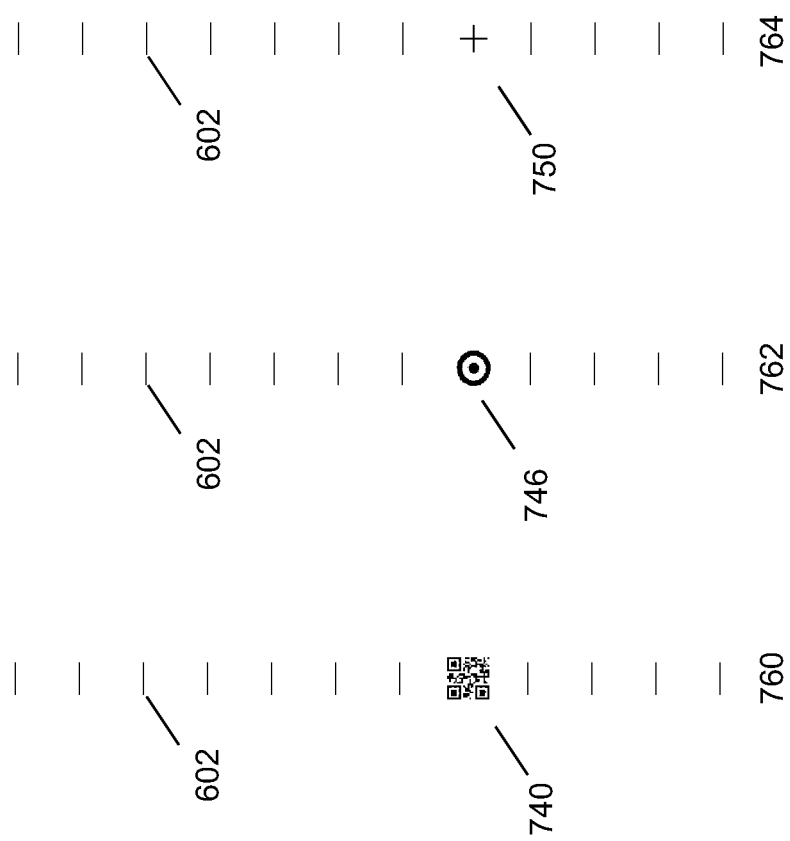
FIG. 14 is a surface view of position and data marks in the context of synchronization marks for use with certain embodiments.

FIG. 14 shows some examples of absolute position or data marks in the context of synchronization marks. Zooming out from a track surface, there may be a large number of synchronization marks 602 repeated at regular intervals, such as every 10 or 20 cm, while absolute position marks 740, 746, and 750 in tracks 760, 762, and 764, respectively, provide an absolute position within the track. In this manner, synchronization marks 602 can be viewed as repeating offsets from a given absolute position.

Similarly, marks 740, 746, and 750 may be dynamic. Mark 740 may be updated to convey data that is individualized to each carrier. Marks 746 and 750 may be dynamically displayed in response to the necessary routing instructions for each carrier, such as telling individual carriers to stop, speed up, slow down, or warn carriers that they are approaching another carrier.

Line Following Navigation

Carrier navigation can be simplified, in some embodiments, by using line following techniques. Line following can allow carriers to include simplified navigational components, while providing robust navigational abilities. For example, two or more photodetectors can be used to observe a line drawn on the track. When these photodetectors are coupled with a controller, such as a PID controller or similar feedback control systems (which may be implemented in hardware or software), along with a means of controlling the direction of the carrier (such as a steering mechanism or multiple drive motors allowing differential steering), a simple and robust system can cause the carrier to follow an arbitrary line drawn on the track. Such systems may have the advantage that components are robust and relatively inexpensive. For example, line following carriers can be implemented using analog components, which may be fast, inexpensive and highly reliable. This may reduce the processor requirements, if any for a carrier to navigate an automation system. In some embodiments, carriers do not need a processor to follow a navigational line drawn on the track. This line may be dynamic and allow the track to direct a carrier along an arbitrarily chosen path. In some embodiments, a controller operating a steering mechanism can be controlled by an onboard processor, as well.

Line following navigation can be implemented using static or dynamic lines drawn on the track. In some embodiments, a portion of the track has static lines, such as along track sections, while decision points, intersections, interaction points, etc. may include dynamic lines. These lines may be redrawn for each carrier to direct the carrier along the track in a desired path.

In some embodiments, a combination of a navigational line and positional or data marks may be used. While the steering of the carrier may be controlled in response to the direction of a line being followed, additional marks, such as landmarks, positional marks, synchronization marks, etc. may be easily detected by a carrier and analyzed by an onboard processor to determine velocity or acceleration profiles for the carrier, as well as stopping points and any data that may be conveyed by marks.

Figure 15:
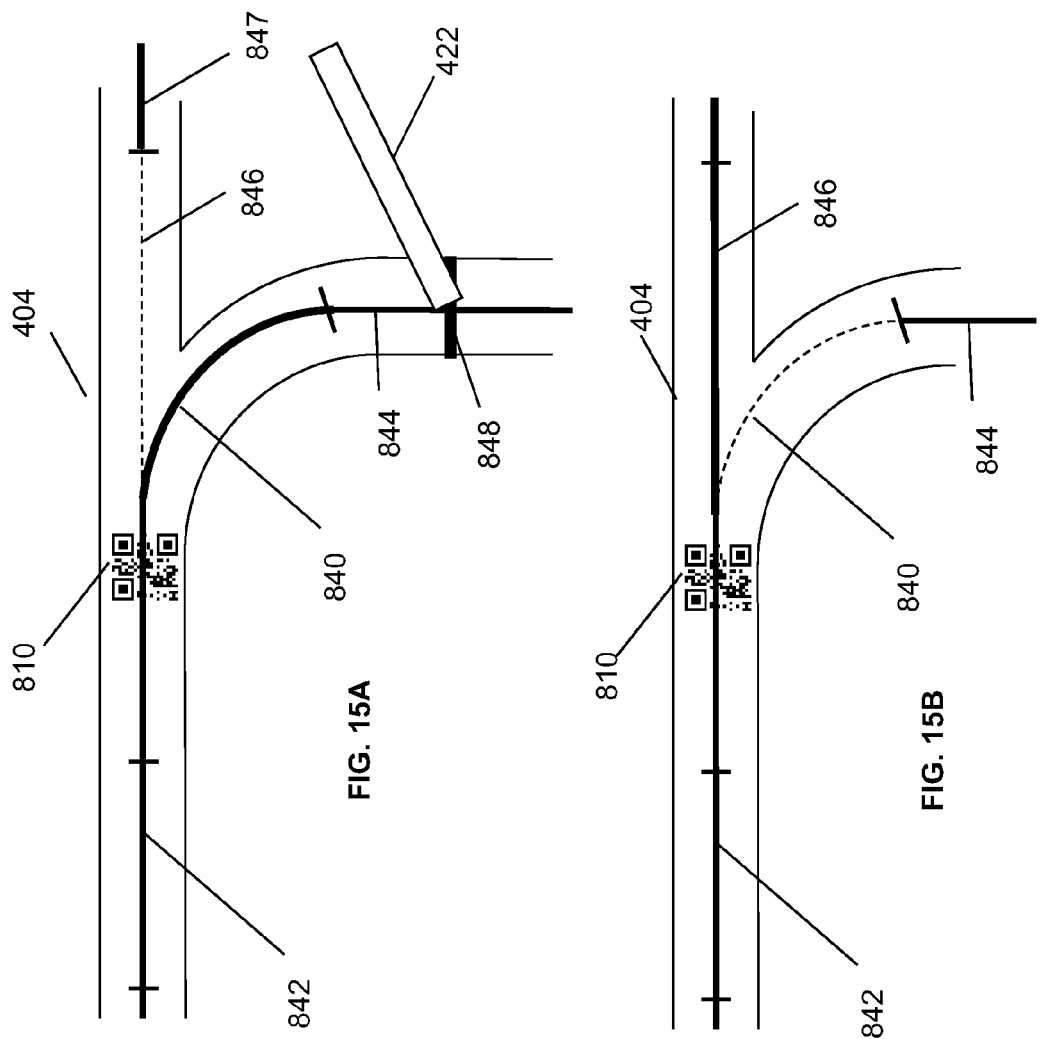
FIGS. 15A and 15B are top views of exemplary track sections employing dynamic marks for routing carriers in certain embodiments.

FIGS. 15A and 15B show an alternate embodiment of the track sections shown in FIG. 12. In these examples, decision point 404 provides a line that a carrier can follow. For example, a carrier with a steering system can traverse the track system by continually following a longitudinal line that indicates the path it should follow. By following this line, which can be changed by an external controller, such as central controller 440 (FIG. 6), the carrier can navigate the track system without the need for mechanical gates. In this example, a carrier can follow a line 842, which may be a static line. For illustrative purposes, line 842 is shown as a solid line, but any other suitable type of line may be used. Upon approaching decision point 404, a carrier will observe absolute position mark 810, which may be a QR code that identifies the upcoming decision point 404. This can be used to alert the carrier that a decision point is eminent and to adjust its trajectory accordingly. Mark 810 can be dynamic and can include trajectory information about the upcoming turn, or instruct the carrier to continue at a higher velocity if the carrier will not be turning.

If the carrier should navigate by turning, as represented in FIG. 15A, line 840 may be illuminated, turned on, or otherwise indicated to the carrier. In some embodiments, a rewritable electronic display, such as an E ink display or an LCD display, can indicate line 840 as a line (shown as a dark line) for the carrier to follow. After traversing line 840, the carrier may encounter a static line 844, which, like line 842, may be permanently drawn on the surface of the track, such as by paint, sticker, or etching. A stop mark 848 may be displayed statically or dynamically to instruct a carrier to stop at the location of the mark to interact with pipette 422. Lines 842, 844, and 847 may be statically or dynamically displayed on the track. For example, the thickness of the line may be used to indicate a speed limit for the track section.

If the carrier should navigate by proceeding straight, as represented in FIG. 15B, line 846 may be illuminated, turned on, or otherwise indicated to the carrier. Like line 840, this indication may be via a rewritable electronic display, such as an E ink display or LCD display. A processor controlling decision point 404 can dynamically switch between displaying a bold or illuminated line 840 and line 846 for each carrier to dynamically issue navigational instruction to each independently movable carrier to move in a predetermined direction (e.g., toward lines 844 or 847).

In some embodiments, mark 810 is a rewritable landmark that also includes a rewritable electronic display. This can allow mark 810 to convey routing information to the carrier, which may indicate whether the carrier should turn, or go straight, or other arbitrary information. In some embodiments, this may be done without requiring the dynamic drawing or highlighting of lines 840 and 846. For example, in some embodiments, a line following system can be instructed as to which branch of a diverging line (e.g., lines 844 or 846) to favor and follow, without requiring these lines to be dynamically drawn. In some embodiments, mark 810 is a simple mark (such as a transverse line) that has only a few states (e.g., binary for turn or straight, or a few bits), allowing it to be read without complicated optics or a camera. For instance, some navigational marks can be viewed with one or more photo detectors.

Figure 16:
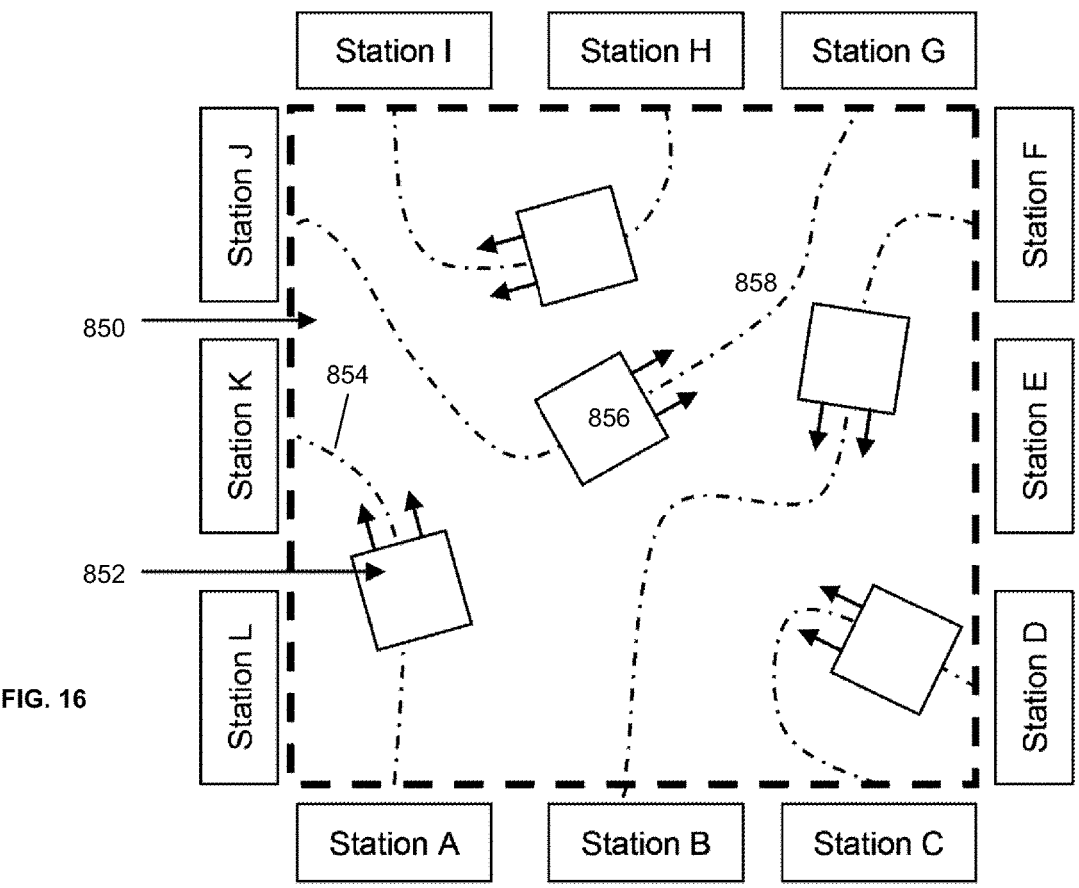
FIG. 16 is a top view of an exemplary two-dimensional surface employing dynamic marks for routing carriers in two dimensions in certain embodiments.

FIG. 16 shows another embodiment that may utilize line following carriers to transport sample vessels between a plurality of stations within an IVD environment. In this embodiment, a two-dimensional surface 850 is provided to allow a plurality of carriers to move two-dimensionally between stations A through L. By utilizing a two-dimensional surface, long one-dimensional tracks can be avoided. One-dimensional track systems typically have certain layout constraints, which may be undesirable for a given laboratory layout. For example, typical tracks in an IVD environment include walls or other mechanical constraints that restrict motion to be substantially one dimensional in character (e.g., the track may curve, etc., but carriers on this typical track move along the longitudinal dimension of that constrained track. Surface 850 substantially lacks one-dimensional constraints in the portion between stations, allowing for arbitrary two-dimensional movement restricted substantially only by the lines drawn to define the one dimensional path a carrier will take (e.g., the line, which may curve or turn, defines a fore and aft direction, and is therefore one dimensional, as the carrier travels along the line). These lines may be drawn in any suitable shape, including straight, curved or geometric.

Typical one-dimensional tracks, such as the track system shown in FIG. 6, include tracks that form large loops, or include long linear portions. For example, a one-dimensional track may allow several stations to be placed along the wall, but as the number of stations increases, the overall length of the automation system increases linearly. Most rooms in buildings are not long rectangular rooms. Accordingly, a linear track system along the wall may not scale properly to the available space in the room. Furthermore, for a linear track, the amount of traffic that must traverse an individual point in the linear track increases with the number of stations and total carriers in an automation system. This may prevent large linear track systems from scaling when a large number of stations or carriers is desired.

Similarly, track systems that use large loops may include a substantial amount of dead space. While a loop-based linear track system can allow stations to be placed in more locations than just along a single wall, the amount of dead space will increase as more stations are added. Furthermore, loop-based track systems often rely on main loops for most traffic routing, which tend to grow in lengths proportional to the number of stations. Traffic on the main loops can increase in proportion to the number of stations (and therefore the more carriers that must traverse the track and the longer they must travel).

Furthermore, linear track systems may introduce large latencies or inter-station transit times as more stations are added. For example, a linear track system that increases from 15 m to 30 m as the amount of stations doubles may result in an average transit that effectively doubles as the average distance that must be traversed doubles in proportion to the number of stations added. Furthermore, the additional traffic that would be needed to service additional stations can add to this latency. It should be appreciated that for most loop-based track systems, the latency and transit times are similarly affected by an increase in the number of stations.

In the system shown in FIG. 16, individual carriers are not constrained to a common linear path. This can allow multiple carriers to traverse a two-dimensional plane in parallel, reducing issues of traffic, and allowing the average distance that a carrier must travel to scale in proportion to the square root of the number of stations for a square layout surface 850. Various other two-dimensional shapes may also be used.

Planar surface 850 can include a rewritable surface that allows lines to be drawn between stations. Carriers equipped with line following hardware can be directed along these lines to carry samples between stations. Collisions can be avoided by ensuring that for any given time segment lines do not cross. This can allow carriers to simply follow the lines without worrying about collisions. This can allow massive parallelism in carrying samples between stations using relatively simple hardware. For example, carrier 852 can follow line 854 between stations A and K. Meanwhile, carrier 856 can follow line 858 between stations J and G. Any suitable rewritable lines may be used. For example, surface 850 can comprise and E-ink or LCD display that allows the plurality of lines to be drawn. Similarly, a projector pointing at surface 850 can project lines via a video projector or a plurality of lasers (or a single laser with multiple or moving mirrors). Similarly, a plurality of LEDs may be embedded in surface 850.

Controlling Local Trajectories

In some embodiments, carriers need not have complicated anti-collision hardware. Whereas some embodiments may include rangefinder hardware to avoid collisions with nearby carriers, optical marks can also be used to simplify collision avoidance with few hardware requirements of carriers. If an automation system can track the location of each carrier and it has a model of the collision avoidance requirements for each carrier, an automation system can use rewritable dynamic marks on the track behind each carrier to inform any trailing carriers that they may be entering a forbidden collision zone for a carrier ahead of it.

Figure 17A:
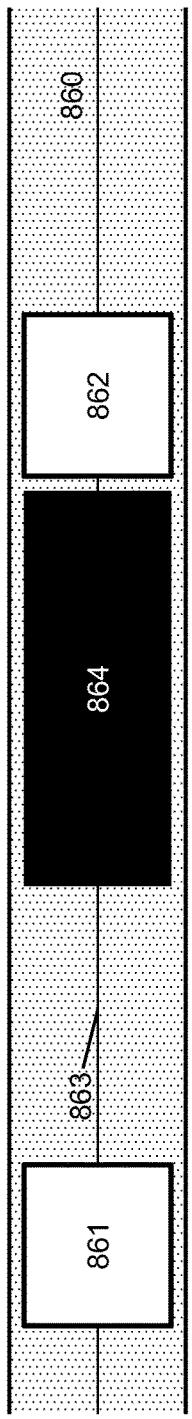
FIGS. 17A and 17B are surface views of exemplary track sections employing dynamic marks for providing collision information to carriers in certain embodiments.
Figure 17B:
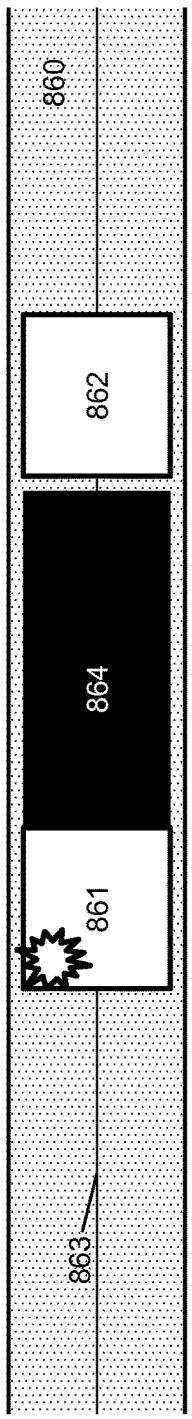

An example of using dynamic optical marks to avoid collisions is shown in FIGS. 17A and 17B. Carriers may travel on a linear track 860. For example, carrier 861 may follow behind carrier 862 following line 863. In response to the presence of carrier 862, a rewritable display or projector may display a collision zone 864 behind carrier 862. This collision zone may follow carrier 862 in substantially real-time. As shown in FIG. 17B, when carrier 861 enters this collision zone, it can detect the presence of mark 864, indicating the collision zone. A processor onboard carrier 861 may respond with evasive action or by issuing a warning to the drive controllers for the carrier.

Figure 18A:
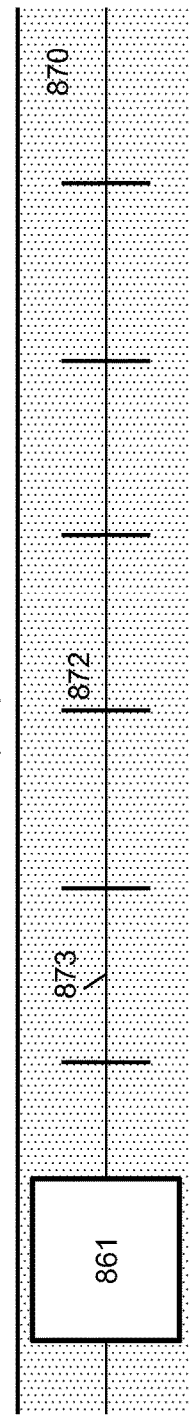
FIGS. 18A and 18B are surface views of exemplary track sections employing dynamic marks for providing collision information to carriers in certain embodiments.
Figure 18B:
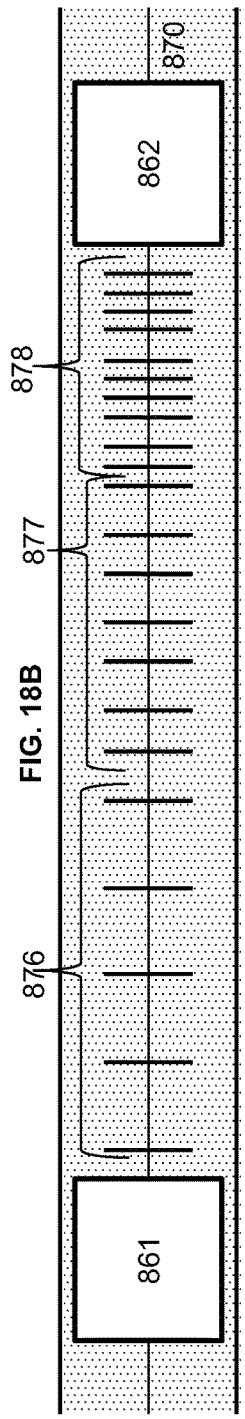

FIGS. 18A and 18B show a similar concept, whereby synchronization marks are used to rate-limit the speed of carrier 861 as it travels along track 870. Carrier 861 encounters synchronization marks 872 as it follows line 870. In FIG. 18A, carrier 861 travels at a high speed as instructed by synchronization marks 872. In FIG. 18B, carrier 861 approaches carrier 862. By detecting the presence of carrier 862 at its position along track 870, the automation system can vary the pitch of trailing synchronization marks displayed on the track. This will instruct carrier 861 to slow down to avoid a collision. In this example, a graduated pitch may be used to vary the speed of a carrier 861 depending on how close carrier 861 is to a collision zone of carrier 862.

For example, when carrier 861 is far away, synchronization marks may be displayed at pitch 876, allowing carrier 861 to proceed at relatively high speed. Once carrier 861 gets nearer to carrier 862, it may encounter synchronization marks with a medium pitch 877, instructing carrier 861 to proceed at a moderate speed. When carrier 861 gets dangerously close to carrier 862, the track may display a finer pitch 878 that instructs carrier 861 to proceed at a slow pace to avoid collision. The pitch may be varied behind carrier 862 in a trailing fashion, allowing the synchronization marks to follow carrier 862, providing persistent graduated pitch to carriers that approach carrier 862.

Figure 19:
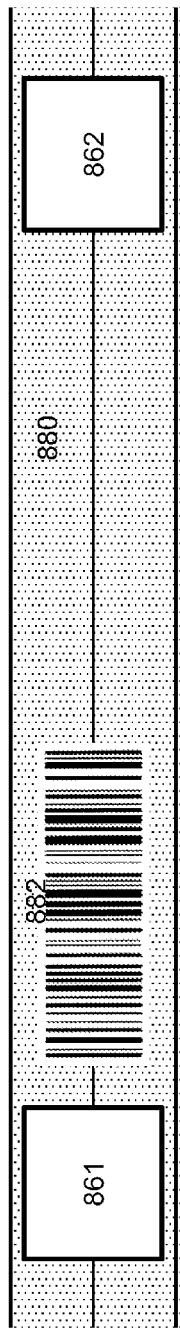
FIG. 19 is a surface view of exemplary track sections employing dynamic marks for providing collision information to carriers in certain embodiments.

FIG. 19 shows another approach to providing warnings to carriers to avoid collisions. As carrier 861 follows carrier 862 along track 880, warnings in the form of barcodes may be provided. Barcode 882 may be displayed to carrier 861 to indicate the distance to carrier 862, allowing carrier 861 to take appropriate action. Barcodes may be provided at regular intervals or be displayed in a trailing fashion, following carrier 862. In some embodiments, barcodes are displayed at regular fixed locations throughout the track to provide collision distance warnings to carriers that pass over these points, allowing track sections between the barcodes to be static, rather than dynamic, to save on manufacturing cost. Provided carrier 861 can estimate its velocity, it may be able to use the real-time instruction or warning in barcode 882 to avoid a potential collision with carrier 862, without requiring real-time distance marks that follow carrier 862.

Figure 20:
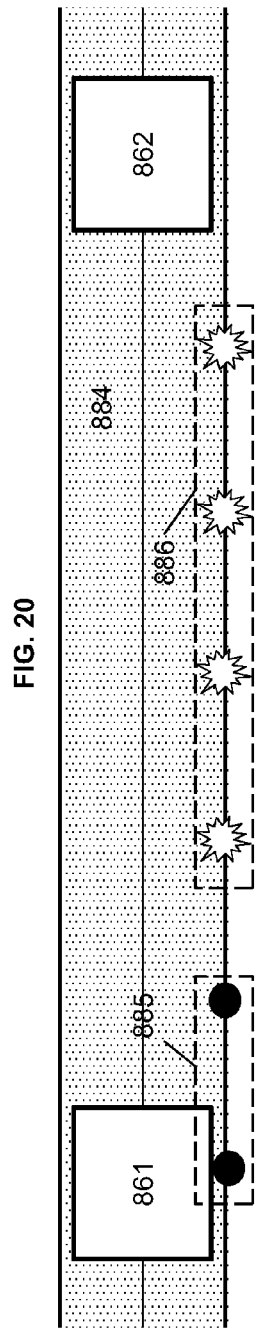
FIG. 20 is a surface view of exemplary track sections employing dynamic marks for providing collision information to carriers in certain embodiments.

FIG. 20 shows another embodiment, whereby optical marks can be used to provide a trailing real-time indication of a collision zone behind carrier 862. As carrier 861 follows carrier 862 along track 884, a plurality of LEDs 886 can be illuminated behind carrier 862 to warn carrier 861 of an impending collision zone. In this embodiment, LEDs may be provided in a track surface, such as along a wall that is visible to carrier 861. LEDs 885 that are outside the collision zone of carrier 862 may be turned off. LEDs 886, that are within the real-time collision zone of carrier 862 may be illuminated in a trailing fashion as carrier 862 moves past additional LEDs. When carrier 861 enters the collision zone of carrier 862, a photodetector or camera on board carrier 861 can notice the illuminated LEDs 886, and an onboard processor may take appropriate action in response to the visual indication that the carrier is in a collision zone, such as slowing the carrier down.

In general, the automation track in the embodiments shown in FIGS. 17A through 20 have some relatively accurate estimation of the location of carrier 862. Having estimation of the location of each carrier can be useful to the automation system. This may allow dynamic markings encountered by each carrier to be tailored to each carrier. In some embodiments, the automation system need only know when a carrier has traversed a given point and the order of carriers, which may be available by observing the order in which carriers check-in at certain points on the track. If the automation system knows the identity of the next carrier that will traverse a given point on the track with dynamic marks, those marks can be updated to provide relevant information to that carrier. The automation system may be able to use a very rough approximation of the location of carriers for most dynamic marks to be useful. In some embodiments, dynamic marks relating to collision zones may require a more accurate estimation of the location of carrier 862 to provide meaningful real-time collision information. As shown in FIG. 19, this information may be obtained via checkpoints. For example, as carrier 862 reaches various checkpoints, barcode 882 can be updated to reflect times at which carrier 862 checks in at given locations throughout the track. In some embodiments, the current location of carrier 862 can be estimated by extrapolation. In some embodiments, overhead cameras, trip lights in the track, or other sensors may be suitable for approximating carrier locations in substantially real-time.

In some embodiments, collision zone information can be provided on the track without requiring a substantially real-time model of the carrier location. For example, carriers can include onboard anti-collision sensors. In another example, carriers may include onboard components suitable for displaying collision information to nearby carriers. For example, a light or laser on the back of a carrier can project a collision zone onto the track behind the carrier. In some embodiments, the additional power requirements required to have light sources on carriers can be avoided.

Figure 21:
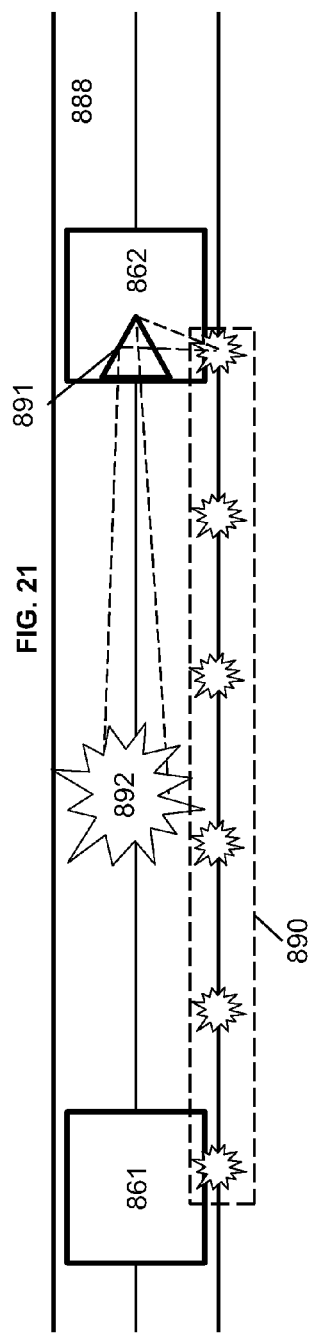
FIG. 21 is a surface view of exemplary track sections employing static reference points for providing collision information to carriers in certain embodiments.

For example, FIG. 21 shows an embodiment whereby passive or static elements in the carrier track may be used to provide dynamic information about a collision zone. In this example, carrier 861 follows carrier 862 along track 888. Track 888 includes a plurality of regularly spaced LEDs 890, which may be always on while the automation system is active. Carrier 862 can include an optical device, such as a mirror or prism 891 that receives light from LEDs 890 as it passes each LED and refracts or reflects this light onto the track to display an image 892 behind the carrier. In this example, as carrier 862 passes each LED, a brief image 892 will flash on the track behind. If carrier 861 encounters image 892 on track surface, a processor on carrier 861 can take evasive action, such as causing the carrier to slow down until image 892 is no longer in the image plane of any optical sensors aboard carrier 861. In embodiments where carrier 862 has active light sources, the behavior of carrier 861 relative to an image received from those light sources can be substantially the same as explained with respect to FIG. 21.

Optical marks can also be used to dynamically instruct carriers where to stop to interact with devices on the automation track, such as pipettes. For example, for each carrier that is scheduled to stop at a pipette, a mark can be dynamically displayed on the track surface before the carrier arrives at the pipette, allowing the carrier to have a reference mark for stopping. In some embodiments, this mark may be co-located with the center of a sample being carried. In these embodiments, the mark may be displayed underneath the carrier or to the side of the carrier, and viewed by optics on the carrier that are co-located with the central axis of a sample tube. In some embodiments, marks may be displayed in front of or behind a carrier, allowing the mark to be displayed via electronically rewritable displays in the track surface or via projection. Each carrier may have optics, such as photodetectors, at the front or back of the carrier. These carriers may be calibrated to stop some distance away from the mark based on the fore or aft observation of the mark.

Figure 22:
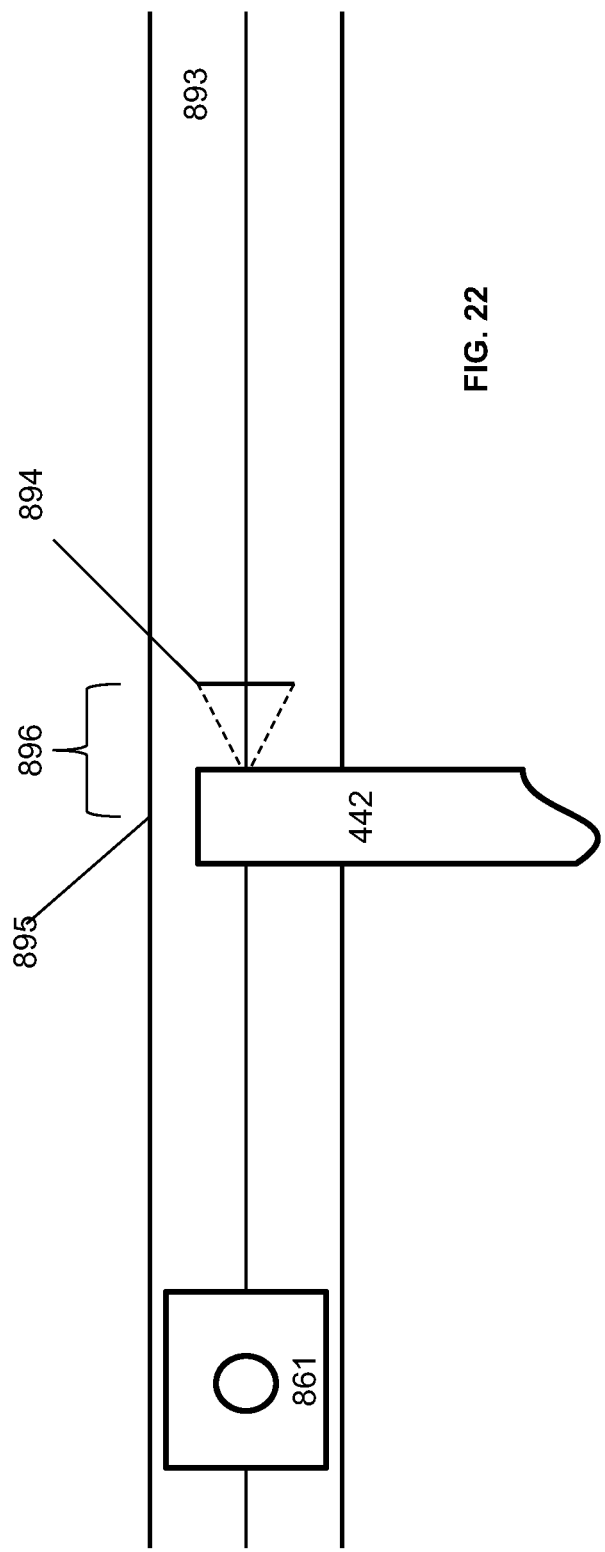
FIG. 22 is a top view of exemplary track sections employing a projected stopping mark at a pipette in certain embodiments.

FIG. 22 illustrates an example of using a dynamic mark to indicate a precise location for a carrier to stop to interact with a pipette. Carrier 861 follows a line on track 893. Carrier 861 is scheduled to stop for interaction with pipette 442. To ensure proper interaction with pipette 442, the center of a sample tube being carried by carrier 861 should stop at position 895. To indicate the location of stopping point 895, pipette 442 projects mark 894 on the track surface coincident with a desired stopping reference to indicate where a carrier should stop to interact with pipette 442. Mark 894 may be projected via a laser and related optics, an LED light source and optics, or a projector that is part of pipette 442 (or more specifically the arm or other mechanism that supports the pipette). Because pipette 442 interacts with a sample tube from above, in this embodiment, mark 894 is projected in front of stopping point 895. This allows optics in the front of carrier 861 to view the track surface having mark 894, without obscuring mark 894 via the shadow of carrier 861. That is, the location of mark 894 may be coincident with a desired interaction point for the pipette, but can be offset from the stopping point by a predetermined amount that reflects the geometry of the carrier viewing the mark.

Because the height of pipette 442 relative to track 893 is repeatable and easily characterizable, the distance 896 between mark 894 and stopping point 895 can also be repeatable and easily characterizable. For example, a carrier can have a well-defined offset between where its optics are pointing and the center point of a sample tube being carried. The carrier can be configured to stop a distance 896 from a stopping mark 894 observed on the track surface.

Using a mark 894 projected from a pipette 442 can have some advantages over using a mark made using a rewritable surface. For example, pipette 442 may have a large lever arm that experiences mechanical drift over time. Over time, the stopping position and encoded position of pipette 442 relative to track 893 can drift. This can be due to wear or other natural phenomena. By utilizing a stopping point that is fixed in relation to the stopping point of pipette 442 once it moves, this may eliminate or reduce the need to calibrate the precise positioning of pipette 442 relative to track 893. Similarly, because track 893 is fixed and pipette 442 may include complex mechanical systems, any errors in aligning these various systems can be accounted for by using a beam projected from an arm holding a pipette 442. This may allow less expensive components to be used in constructing the arm that moves pipette 442 relative to track 893. This can result in a more robust system.

In some embodiments, a characterization station may be used to calibrate the particular spatial relationship between where the optics of carrier 861 point and the line of action of the center of a tube carried by carrier 861. In some embodiments, a characterization station, such as the characterization station described in co-pending application Siemens reference number 2012P23219US, which is incorporated herein by reference, may be used to characterize any offsets that should be used when interacting with carrier 861. In some embodiments, the location of mark 894 relative to the stopping position of pipette 442 may be adjustable for each carrier. Based on the characterization of each carrier, distance 896 may be adjusted when displaying mark 894. Similarly, distance 896 between a reference mark on track 893 and a stopping position 895 may be adjusted when using rewritable displays in the surface of track 893. For example, each carrier may have an individual calibrated distance 896 that reflects the difference in the location of the center of a sample tube being transported and the location on the track surface relative to that center position that the optics on the carrier point. Carrier 861 may be characterized, such as via a characterization station or via a calibration of the known values for a given type of carrier, to determine an estimate of distance 896 that should be applied when pipette 442 interacts with carrier 861. Mark 894 may be displayed via rewritable surfaces in track 893 or via a beam projected by pipette 442 at a position that places the mark 894 on track 893 a distance 896 from the desired stopping point 895 for the center of a sample tube being transported by carrier 861.

Exemplary Hardware for Optical Based Navigation and Control

Figure 23:
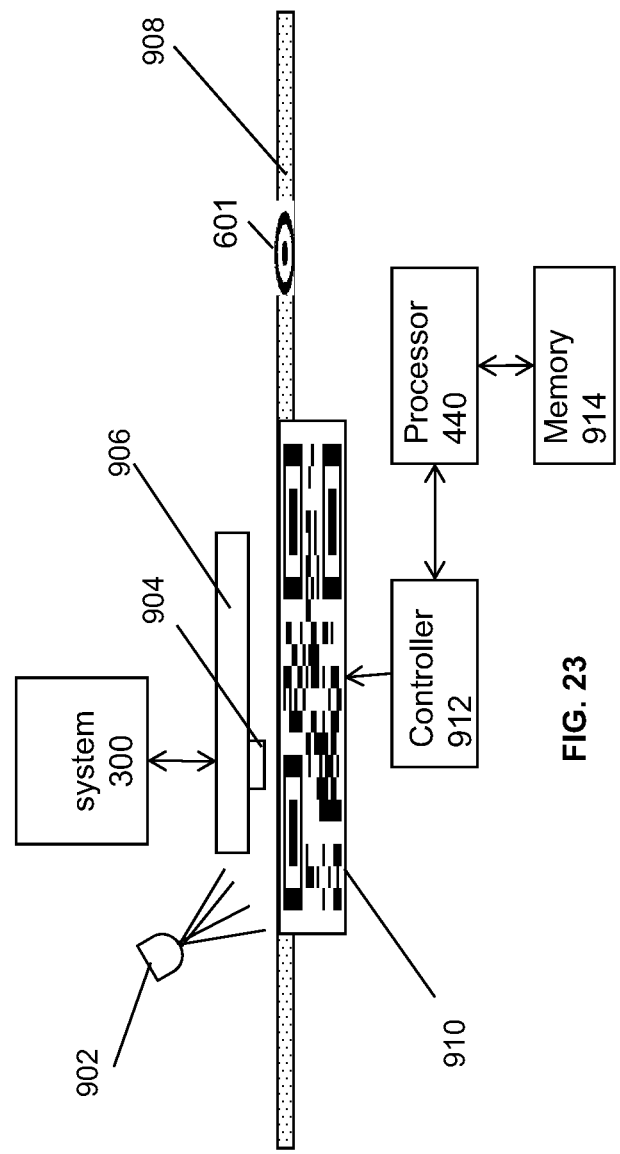
FIG. 23 is a system diagram depicting an exemplary system for displaying dynamic marks on a track surface.

In the example shown in FIG. 23, a dynamic mark 910 can be observed by image sensor 904. A light source 902 can be provided in the form of an LED or other light source off axis from or coaxially to image sensor 904. By providing illumination off axis, which may include illumination at a steep angle relative to surface 908, the light source 902 can create shadows within surface 908 to accentuate any surface textures. This may allow image sensor 904 to observe additional information about a track besides reading dynamic marks, such as mark 910 or static marks on the surface, such as mark 601. In some embodiments, image sensor 904 can also be used to observe relative motion of marks or pitting in surface 908 to provide real time observation of velocity and trajectory. Image sensor 904 may include optics, such as lenses to properly observe the image of track surface 908, and one or more sensors, such as photo detectors, CCD sensors, or digital imaging devices to capture images of the surface at regular intervals in real time. An image processor 906 may be coupled to image sensor 904 to decode the signals from image sensor 904 and provide image data to system 300. In some embodiments, image processor 906 and image sensor 904 supply real-time trajectory information to system 300, in addition to providing information about data contained in dynamic mark 910 and static mark 601. In other embodiments, image sensor 904 may simply provide data related to marks.

Dynamic mark 910 can be, for example, a QR code created by an electronically rewritable surface. This electronically rewritable surface can be any suitable rewritable surface, such as an E-ink display, an LCD display, an AMOLED or OLED panel, or an array of LEDs. In some embodiments, the size of a mark can be larger than the image field of sensor 904. In some embodiments, the track surface can be passive and marks can be displayed using an overhead-mounted projector. This may allow the costs to be decreased, as a single global or local projector can be used, rather than requiring track sections to include electronic displays. In some embodiments, the projector can be a rear-projection display, allowing a projector to be mounted behind a track surface, such that a translucent passive surface can display information to a carrier.

Because image sensor 904 moves longitudinally, the length of a position mark can still be observed using a smaller imaging sensor because the imaging sensor will eventually traverse the entire mark. To the extent that a position mark is wider than the image field of an imaging sensor, multiple image sensors may be employed and the images can be stitched together. It is contemplated that multiple imaging sensors can be used in certain embodiments to provide added robustness of observing textures (e.g., providing stereoscopic or redundant vision) or position marks. Multiple imaging sensors, such as an array of imaging sensors, can also be used to observe larger position marks, while also providing robustness in observing real-time relative motion of the track surface to the carrier. In some embodiments, a separate image sensor or sensors may be used to read marks, while another sensor may be used to observe the relative motion of the track surface.

Electronically rewritable mark 910 can be operated via a controller 912, which may provide parallel or serial communication to transistors driving each pixel, such as by providing row and column data. Controller 912 may be responsive to a processor, such as central control processor 440, which can allow a central processor to choose which information to convey to a given carrier on a real-time basis. The processor 440 may be responsive to instructions and data in memory 914, which may include a database of potential QR codes as well as a database of carrier information to determine what general information to display, and how to display it. In some embodiments, the processor used to interact with controller 912 is a local processor that is separate from central control processor 440, and may, in some embodiments, be responsive to another processor, such as the central processor.

Figure 24:
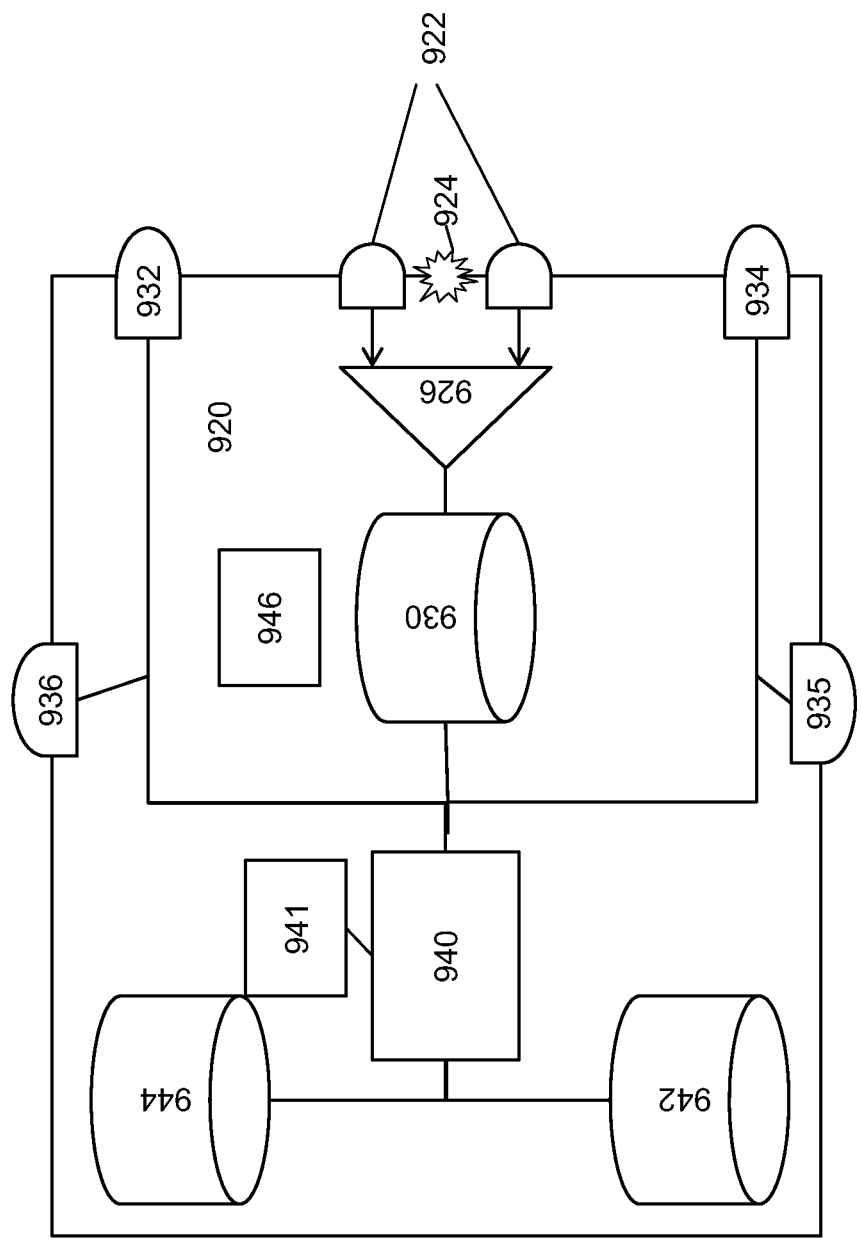
FIG. 24 is a system diagram depicting an exemplary carrier for use with some embodiments.

Controlling carriers using the dynamic and static optical marks can greatly simplify the components used in constructing carriers. FIG. 24 shows an exemplary simplified carrier 920 that may be used with optical mark control. Carrier 920 can include a plurality of optical sensors, a processor, power system, and at least a steering mechanism to successfully navigate an automation system, receiving information from the automation system by reading marks and navigating based on the line following. Exemplary carrier 920 can be compared and contrasted to system 300 in FIG. 5. Embodiments of the carriers suitable for use with optical navigation and control can include carriers having any subset of the systems shown in FIG. 24 or FIG. 5. In some embodiments, carriers are greatly simplified as shown in FIG. 24, while in other embodiments, additional complexity and features may be added by using components shown in FIG. 5.

A plurality of photodetectors 922 can be used to follow a navigation line on a track. An optional light source 924 may illuminate the line to allow photodetectors 922 to observe the position of the line relative to the carrier. Photodetectors 922 may include two or more photodetectors placed in a line or array to aid in interpreting the line. Signals detected by photodetectors 922 may be interpreted by detector circuit 926. In some embodiments, detector circuit 926 may be substituted using software in the processor. In some embodiments, detector circuit 926 can be a DSP or analog circuit.

In some embodiments, detector circuit 926 may be a comparator that provides an analog or digital comparison of signals from photodetectors 922. By comparing signals from laterally spaced photodetectors, detector circuit 926 may produce an error signal that indicates the position of a line on the track relative to a center point of photodetectors 922. This signal from detector circuit 926 may be fed to a processor or may be fed directly to a steering mechanism 930, to direct the carrier to minimize deviation from the line. In some embodiments, photodetectors 922, detector circuit 926, and steering mechanism 930 provide a feedback loop for real-time control, allowing the carrier to substantially follow a line in the track. In some embodiments, detector circuit 926 may include control circuitry, such as a PID controller, to enhance stability.

Additional image sensors may include a plurality of photodetectors or imaging devices, such as devices 932-936. In this example, sensors 932 and 934 comprise photodetectors spaced away from photodetectors 922. This may allow sensors 932 and 934 to detect navigational marks in the track surface. For example, marks to the side of a central line may indicate the need to turn in a direction or prepare to turn in a direction. Similarly, lateral marks may indicate a stopping point. Sensors 932 and 934 may be suitable for detecting these navigational marks. In some embodiments, sensors 932 and 934 may also be suitable for detecting data marks. For example, detectors 932 and 934 may be suitable for reading a barcode that comprises lateral marks. An array of sensors can be used to read larger navigational or data marks, such as QR codes and two-dimensional patterns.

Sensors 936 and 935 may be used to read optical marks on other surfaces, such as walls. This may allow additional placement of navigational or data marks. Sensors 935 and 936 may include photodetectors or imaging devices, as appropriate to the application.

Sensors can communicate with processor 940, allowing processor 940 to interpret any navigational marks in the data contained in any data marks. In this manner, sensors 932 through 936 can be used as a communication system, whereby processor 940 receives data and instruction from an automation system. This may eliminate the need for RF communication in some embodiments. In some embodiments, carrier 920 may only receive information from an automation system, but may not transmit information. In some embodiments, carriers may include passive or active RFID tags suitable for conveying carrier identity information. Processor 940 may be coupled to memory 941, which may include data and instruction memory.

Once processor 940 has interpreted any navigational data marks, processor 940 may control drive mechanisms in the carrier to respond to data or navigational marks. For example, processor 940 may drive wheels, such as wheels 942 and 944, in some embodiments, wheels 942 and 944 may operate differentially, allowing them to operate as a steering mechanism. In some embodiments, steering mechanism 930 can be eliminated by using differentially operated wheels. Carrier 920 can include an onboard power source, such as a battery 946.

Figure 25:
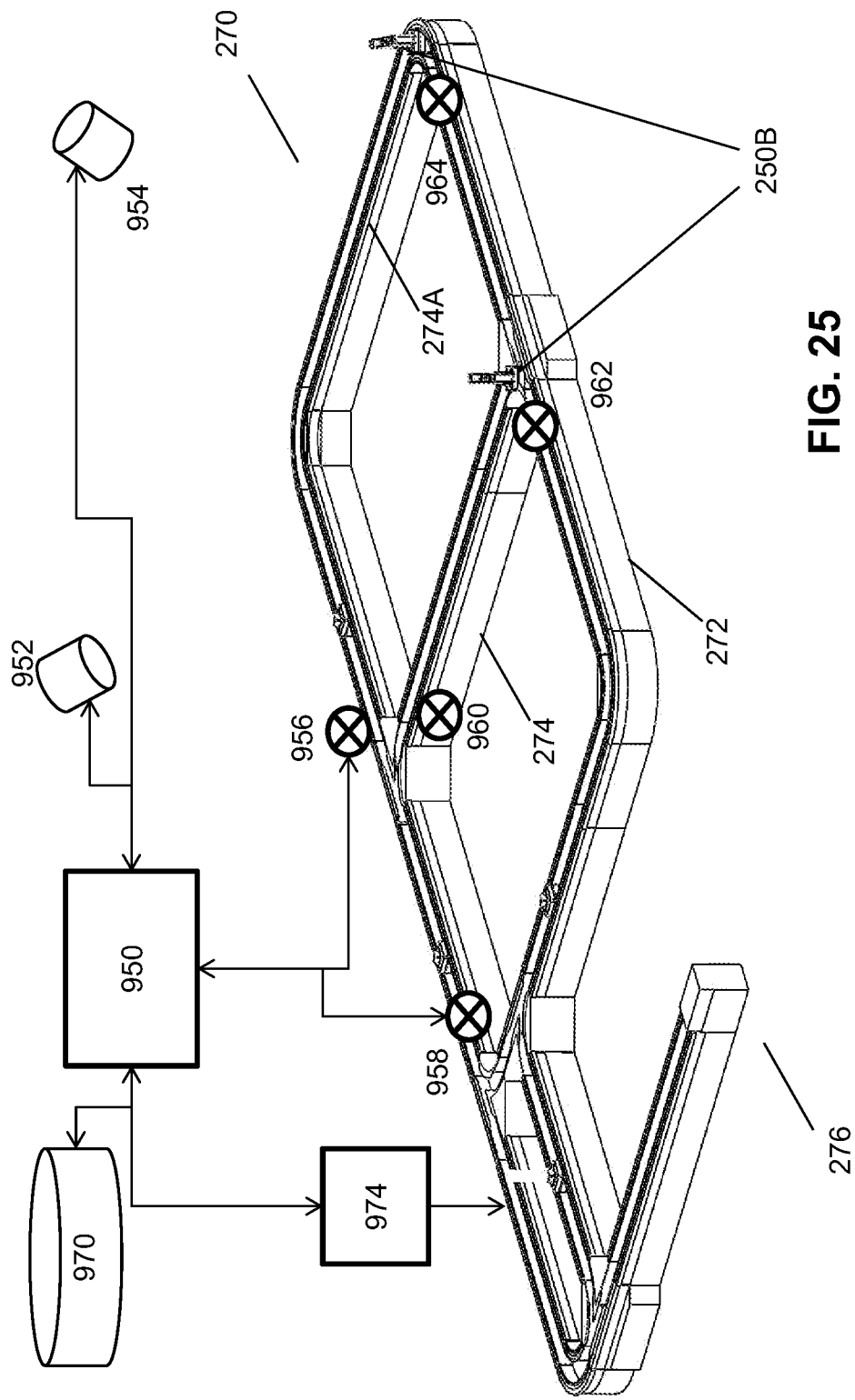
FIG. 25 is a system diagram depicting an exemplary system for tracking carriers and displaying dynamic marks on a track surface.

FIG. 25 shows a system diagram of the control systems that may be used with automation system 270. Automation system 270 can include a track system that includes track sections 272, 274, 274A, and 276. A plurality of carriers 250B can traverse the automation system. An automation system processor 950 can observe the locations and/or trajectories of carriers 250B and issue navigational instructions and data to these carriers.

In some embodiments, to exhibit navigational control and send data to carriers, processor 950 communicates with a plurality of sensors that may provide substantially real-time information about the location and trajectory of these carriers. In some embodiments, sensors that track carriers can include one or more cameras, such as overhead cameras 952 and 954. Overhead cameras can allow real-time tracking of a plurality of carriers, using few cameras. Carriers can include top-facing optical marks that identify them to the camera, such as IDs. In some embodiments, cameras can track objects without visual identification of the identity of each object. In some embodiments, sensors, such as checkpoints on the track, may include RFID readers or other sensors to identify individual carriers, can determine the ID of these carriers to initialize a location model of carriers within the automation system. A processor receiving subsequent or concurrent images from overhead cameras can correlate the identities of individual carriers with objects appearing in images from overhead. For example, as a carrier passes a checkpoint, that carrier's identity can be correlated to an object that is observed coincidentally passing that checkpoint location in an image of the automation track. In some embodiments, checkpoints are only used to initialize object tracking, allowing imaging to subsequently track carriers in real time.

Sensors may also include a plurality of checkpoints, such as checkpoints 956 through 964. These checkpoints may include cameras that observe visual marks, such as barcodes, on each carrier to identify the carrier or RFID readers that identify carriers that pass the location of each checkpoint. In some embodiments, checkpoints may include a light sensor that detects an object passing by. If a controller for the automation track has a rough idea of the location or order of carriers traversing an automation track, simple checkpoints that identify when an object passes may provide enough information to correlate the location of individual carriers with the time at which an object passed the checkpoint. This can provide a near real-time estimate of the exact location of each carrier in the automation system by using extrapolation techniques or interpolation techniques between checkpoints.

By using checkpoints or visual tracking of individual carriers, an automation system may be able to alter dynamic optical marks in the track to interact with these carriers. For example, when a carrier passes checkpoint 960, dynamic marks on track section 274 may be updated to convey data or navigational instructions to that carrier.

Sensors 952 through 964 can send information to central processor 950. Central processor 950 can interpret the sensor information to provide substantially real-time tracking of individual carriers. It should be appreciated that any subset of sensors may be used that is suitable for providing near real-time or substantially real-time tracking of individual carriers in this embodiment. Once processor 950 has determined the location of individual carriers, processor 950 can record their location in database 970. Processor 950 may also consult database 970 to review work orders for each carrier, and determine the navigational steps that may be necessary for directing each carrier to its next scheduled location. Once the navigational steps have been determined for each carrier, processor 950 may interact with controller 974 to update individual navigational marks in track system 270. This may include updating rewritable lines for each carrier to follow in upcoming track sections or any other technique discussed throughout. Processor 950 may also interact with controller 974 to convey data to individual carriers using dynamic marks.

While the invention has been described with respect to transporting samples, the methods and systems discussed herein can also be used to transport other items in an IVD environment. For example, the item being transported can be a patient sample, one or more reagents for use with sample analysis, or waste products, such as spent reagent cartridges, used samples, or the like. Reagents can be transported on carriers that are similar to those used for transporting samples. In some embodiments, the bracket supporting the item, such as bracket 262 in FIG. 4A, is adapted to the item being transported. For example, the bracket can be molded to receive a reagent cartridge and securely transport it around the automation system between stations, such as a reagent storage station and a testing station, where the testing station can use the reagent. It should be appreciated that carriers can be adapted to transport any suitable item using the methods and systems described herein.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention, and that such changes and modifications may be made without departing from the true spirit of the invention. It is therefore intended that the appended claims be construed to cover all such equivalent variations that fall within the true spirit and scope of the invention.

What is claimed:

1. An automation system for use with an automated clinical chemistry analyzer comprising:
   one or more surfaces of an automation track configured to dynamically display a plurality of optical marks;
   a plurality of independently movable carriers configured to move along the one or more surfaces and observe them to determine dynamic navigational information from the plurality of optical marks and to alter a trajectory of each carrier in response to the navigational information; and
   a processor configured to dynamically update content of the plurality of optical marks to dynamically convey information that pertains to each respective independently movable carrier, including information to instruct each carrier where to go in the automation system.

2. The automation system of claim 1, wherein the plurality of marks comprise at least one two-dimensional optically encoded mark.

3. The automation system of claim 1, wherein the plurality of marks comprise at least one barcode oriented in a direction of travel of the plurality of independently movable carriers.

4. The automation system of claim 1, wherein the plurality of marks comprise at least one line configured to be followed by one or more of the plurality of independently movable carriers, wherein the line changes to dynamically instruct each carrier to move in a predetermined direction.

5. The automation system of claim 4, wherein at least one of the one or more surfaces is substantially unconstrained in two dimensions, facilitating arbitrary two-dimensional movement defined by the at least one line.

6. The automation system of claim 1, wherein the plurality of marks comprise marks that dynamically convey data to the plurality of independently movable carriers.

7. The automation system of claim 1, wherein each of the plurality of independently movable carriers comprises:
   one or more optical sensors; and
   at least one processor configured to control the motion of the carrier in response to the plurality of optical marks.

8. The automation system of claim 1, wherein the one or more surfaces are further configured to statically display a plurality of static optical marks.

9. The automation system of claim 1, wherein the plurality of marks comprise marks indicating a collision zone of at least one of the plurality of independently movable carriers.

10. The automation system of claim 1, wherein at least one of the plurality of marks comprises a mark that is dynamically displayed on one of the track surfaces at a location coincident with the location of a pipette.

11. A carrier configured to travel along an automation surface for use with an automated clinical chemistry analyzer comprising:
    one or more optical sensors for observing a plurality of optical marks on the automation surface, wherein content of optical marks is dynamically updated by a central controller to convey information that pertains to each respective carrier, including information to instruct each carrier where to go in the automation system; and
    at least one processor configured to determine navigational information from the optical marks and to control the trajectory of the carrier in response to the optical marks.

12. The carrier of claim 11, wherein the processor is further configured to receive non-positional data from the optical marks.

13. The carrier of claim 11, wherein the carrier is further configured to observe one or more marks on the first surface to determine a stopping point in the automation surface.

14. The carrier of claim 11, wherein the at least one processor is further configured to control the carrier to follow a dynamic line.

15. The carrier of claim 11, wherein the at least one processor is further configured to determine if the carrier is at risk of colliding with another carrier from the optical marks.

16. The carrier of claim 11, wherein the carrier is further configured to observe one or more synchronization marks on the first surface of the track.

17. The carrier of claim 11, wherein the carrier lacks an RF receiver for receiving information from an automation system.

18. The carrier of claim 11, further comprising an RFID tag to identify it to an automation system.

19. An automation system for use with an automated clinical chemistry analyzer comprising:
    a plurality of track sections configured to facilitate travel between a plurality of locations in the automation system;
    a plurality of electronically rewriteable surfaces on each of the plurality of track sections configured to dynamically display navigational marks to a plurality of carriers that traverse the automation system;

at least one of one or more optical sensors and RFID scanners configured to determine at least the current track section of the plurality of carriers; and one or more processors configured to update information displayed by the electronically rewriteable surfaces to convey individualized information to individual carriers as they traverse the automation system, including information to instruct carriers where to go in the automation system.

20. The automation system of claim 19, wherein the plurality of electronically rewriteable surfaces comprise an LCD or E-ink display.

21. The automation system of claim 19, further comprising a characterization station configured to characterize the location of a sample being carried by each carrier relative to the rest of the carrier.

\* \* \* \* \*